United States Patent [19]
Walling et al.

[11] Patent Number: 5,962,670
[45] Date of Patent: Oct. 5, 1999

[54] PROMOTERS FOR ENHANCING PLANT PRODUCTIVITY

[75] Inventors: Linda L. Walling, Claremont, Calif.; Véronique Pautot, Gif sur Yvette, France; Yong-Qiang Gu, West Lafayette, Ind.; Wun Shaw Chao, Pullman, Wash.

[73] Assignees: The Regents of the University of California, Oakland, Calif.; Institut National de la Recherche Agronomique, Paris, France

[21] Appl. No.: 08/892,770

[22] Filed: Jul. 15, 1997

[51] Int. Cl.$^6$ .............................. C12N 15/82; C12N 5/04; C12N 15/29; A01H 4/00
[52] U.S. Cl. .......................... 536/23.6; 536/24.1; 800/287
[58] Field of Search ................................ 536/23.6, 24.1; 800/205, DIG. 15

[56] References Cited

PUBLICATIONS

Abel, et al., *Science* 232:738 (1986).
Gurley, et al., *Mol. Cell. Biol.* 6:559 (1986).
Vacek, et al., *Nature* 328:33 (1987).
Walling, et al., *Nuc. Acids Res.* 16:10477 (1988).
Pautot, et al., *Mol. Plant–Microbe Interact.* 4:284 (1991).
Chang & Walling, *Plant Mol. Biol.* 19:217 (1992).
Datta, et al., *Plant Mol. Biol.* 20:619 (1992).
Hildmann, et al., *The Plant Cell* 4:1157 (1992).
Pautot, et al., *Proc. Natl. Acad. Sci. USA* 90:9906 (1993).
Anderson, et al., *Plant Physiol.* 105:331 (1994).
Gu, Ph.D. Thesis, University of California, Riverside, CA (1994).
Gu, et al., *Plant Physiol.* 105(1 Suppl.):46 (1994).
Shiota, et al., *Plant Physiol.* 106:17 (1994).
Aono, et al., *Plant Cell Physiol.* 36:1687 (1995).
Hattori, et al., *Mol. Gen. Genet.* 246:419 (1995).
Schaller, et al., *Plant Cell* 7:1893 (1995).
Walling et al., *J. Cell. Biochem.* Supplement (19A) p137 (1995).
Chao, et al., *Plant Physiol.* 111(2 Suppl.):121 (1996).
Gu, et al., *J. Biol. Chem.* 271(42):25880 (1996).
Gu, et al., *Plant Physiol.* 110:1257 (1996).
Gu, et al., *Plant Physiol.* 111(2 Suppl.):48 (1996).
Walling & Gu, Plant Aminopeptidases: Occurrence, Function, and Characterization, in Aminopepidases, Taylor (ed), (1996) pp173–219.
Laloi, et al., *Nature* 389:135 (1997).
Kim et al. Plant Molecular Biology. 1994. Vol. 24: 105–117.
Matzke and Matzke. Plant Physiol 1995 vol. 107: 679–685.
Milligan and Gasser. Plant Molecular Biology. 1995, vol. 691–711.
McElroy et al. The Plant Cell. 1990 vol. 2: 163–171.
Burley et al. Proc. Natl. Acad. Sci. vol. 1990 87: 6878–6882.
Accession No.: 112756.
Fillati et al. Bio/Technology. 1987 vol. 5: 726–730.

*Primary Examiner*—Douglas W. Robinson
*Assistant Examiner*—Ousama Zaghmout
*Attorney, Agent, or Firm*—Townsend and Townsend and Crew LLP

[57] ABSTRACT

Tomato LapA promoters and gene sequences are provided. The promoters are induced in plants upon wounding, or other stress-related conditions. The gene sequences include a full-length LapA gene, particularly the amino terminal region of the gene. Methods of making stress resistant plants, and of making plants susceptible to stress are provided.

18 Claims, No Drawings

PROMOTERS FOR ENHANCING PLANT PRODUCTIVITY

FEDERALLY SPONSORED RESEARCH OR DEVELOPMENT

This invention was made with Government support under Grant No. IBN9318260, awarded by the National Science Foundation. The Government has certain rights in this invention.

BACKGROUND OF THE INVENTION

Peptidases have a central role in the degradation of proteins by hydrolyzing peptide bonds. For a review of peptidases see, Walling, L. L. & Gu, Y.-Q., AMINOPEPTIDASES, Taylor, A., ed, R. G. Landes Co. (1996), herein incorporated by reference. Based on the reaction catalyzed, these enzymes can be classified as endopeptidases, carboxypeptidases or aminopeptidases. Aminopeptidases cleave single amino acid residues at the free N-termini of peptides or proteins.

Aminopeptidases are ubiquitous enzymes with a wide variety of activities detected in animal, plant and prokaryotic cells. In plants, aminopeptidases have been implicated in the mobilization of storage proteins, the salvage of C and N from dying cells, and in the activation and inactivation of regulatory molecules, including peptide hormones and peptides involved in cell-cell interactions. The expression of some aminopeptidases have been found to relate to a plant's response to mechanical wounding, pathogen infestation and other environmental stimuli.

Aminopeptidases traditionally have been distinguished from each other by the N-terminal amino acid cleaved by the enzyme. Leucine aminopeptidase (LAP) was first characterized from bovine lens by Hanson, H., et al. in *Z. Physiol. Chem.* 348(6):689 (1967). Plant LAP cDNA has since been generated from Arabidopsis, potato and tomato.

In addition to substrate specificity, plant aminopeptidases, including LAP, can be characterized by their optimal pH for enzymatic activity (Mikola, L. & Mikola, J., PLANT PROTEOLYTIC ENZYMES, VOL. II, Dalling, M. J., ed., CRC Press, Boca Raton, Fla. (1986). While LAPs with pH optima in the neutral and alkaline pH ranges have been known, only recently have acidic LAPs been discovered. Two distinct cDNA's encoding acidic leucine aminopeptidase (LAP-A) were generated from tomato (Gu, Y.-Q., et al.,*J. Biol. Chem.* 271(42):25880 (1996), herein incorporated by reference). The deduced genes for these separate proteins were found to be tightly linked and therefore named LapA1 and LapA2. The entire gene sequences were found to share 93% homology but only two amino acid substitutions were within the coding region. The LAP-A enzyme was found to be large, greater than 327 kD, with monomers of 55 kD and a pI of 5.9. Neutral leucine aminopeptidases of 55 kD and LAP-like proteins of higher molecular weight were also found in tomato leaves after wounding but these proteins were also present in healthy tissue and therefore do not appear to be related to wounding or exposure to environmental stimuli. As further proof of the divergence between LAP-A and the other LAP proteins, genomic DNA blots of both types of Lap genes do not cross-hybridize under reduced stringency hybridization conditions.

A model for mechanical plant wounding has been developed (Hildmann, T., et al., *The Plant Cell* 4:1157 (1992), herein incorporated by reference. The authors found that exogenous addition of the phytohormones, abscisic acid (ABA) and methyl jasmonate (MeJa), induced strong accumulation of LapA mRNA in the leaves of potatoes as well as other transcripts of genes activated by mechanical wounding or pathogen infestation, including proteinase inhibitors I and II. They hypothesized that endogenous ABA and MeJa are involved in mediating the systemic response to wounding. In tomatoes, Pearce, G., et al. in *Science* 253:895 (1991) discovered systemin, a peptide signal which mediates the systemic response to wounding by increasing proteinase inhibitor transcripts in leaves. More recently, MeJa has been used successfully to differentially induce LapA mRNA in tomato leaves (Gu, Y.-Q., et al., *J. Biol. Chem.* 271(24):25880 (1996).

Promoters are non-transcribed regions of nucleic acid which bind RNA Polymerase II and direct transcription of mRNA. For a general discussion of promoters, see Lewin, B., GENES, 5TH ED., Oxford University Press (1994) chap. 29, of which the relevant discussion of promoters is incorporated by reference.

A simple eukaryotic promoter includes the dinucleotide CA motif surrounded by pyrimidines; $Py_2CAPy_5$. This sequence lies at the start point of transcription (−3−+5) and is termed the initiation sequence. However, most promoters consist of other sequences that bind transcription factors which modulate the action of RNA Polymerase II. The more common sequences found in promoters are the TATA box, found at approximately position −25, and at about 100 base pairs upstream from the start point, consensus sequences CAAT, GGGCGG and/or ATTTGCAT. It is not necessary for promoter sequences to contain all of these sequences, but virtually all eukaryotic promoters contain at least one of the above sequences.

Typically, an expression cassette to be introduced into a transgenic plant contains the nucleic acid sequence to be transcribed and a promoter to direct the transcription. The promoter can either be homologous, i.e., occurring naturally to direct the expression of the desired transgene or heterologous, i.e., occurring naturally to direct the expression of a nucleic acid derived from a gene other than the desired transgene. Fusion genes with heterologous promoter sequences are desirable, e.g., for regulating expression of encoded proteins. In some instances, the promoter may constitutively bind transcription factors and RNA Polymerase II. In other instances, a heterologous promoter may be desirable because it has sequences that bind transcription factors the naturally occurring promoter lacks.

As described, tomato LapA promoters are induced by a variety of stressful conditions. Therefore, isolated and identified LapA promoters from tomato would be desirable, e.g., for directing expression of heterologous proteins, in transgenic plants under environmental stress. The present invention provides for these and other features.

SUMMARY OF THE INVENTION

This invention relates to use of plant promoters which are activated upon wounding to direct the expression of tomato acidic leucine aminopeptidase. In a plasmid or other suitable expression cassette, the nucleic acid sequence of the promoter is placed upstream of a heterologous nucleic acid such as the coding sequence of a protein, the expression of which is desired upon wounding or other environmental stimuli. The expression cassette is then introduced into a transgenic plant with the result that it exhibits certain characteristics, such as enhanced survival, production of sap (or syrup), flowering, etc. upon environmental stimuli such as wounding, high salinity, freezing, or drought.

In one class of embodiments, the present invention relates to recombinant nucleic acid constructs comprising plant acidic leucine aminopeptidase promoters capable of being activated by wounding. The promoters hybridize under stringent conditions to SEQ ID NO:1 or SEQ ID NO:3. These promoters can be used to direct the expression of certain homologous genes when a transgenic plant is wounded, either mechanically, chemically, by pathogenic infection, or insect infestation.

The nucleic acid constructs of this invention can further comprise foreign nucleic acid sequences that encode proteins which confer certain characteristics, such as enhanced survival, production of sap (or syrup), flowering, etc., upon the plant when wounded or when undergoing various types of environmental stimulus, such as drought, freezing, or salinity. The foreign nucleic acid and the promoter of this invention can be part of an expression cassette which comprises other regulatory elements, including additional promoter sequences, enhancer elements, initiation and stop codons, stabilizing splicing junctions, polyadenylation sequences, and other transcription or translation-modulating sequences known in the art.

This invention also relates to recombinant nucleic acid sequences that hybridize to nucleic acid sequences that encode the full-length, and particularly amino acid residues 1–102, of LapA, a protein expressed in tomato plants after wounding. Unlike neutral leucine aminopeptidase which is expressed in plant tissues without wounding, acidic leucine aminopeptidase is systemically expressed, in the plant's organs, greater than 100-fold after wounding the plant. This invention also relates to an isolated polypeptide encoded by recombinant nucleic acid sequences identified as the full-length tomato acidic leucine aminopeptidase coding sequence. Furthermore, the invention encompasses molecular tags which allow for the isolation and purification of the tomato acidic leucine aminopeptidase.

Also encompassed by this invention are recombinant nucleic acid sequences that hybridize to the full-length genomic tomato acidic leucine aminopeptidase gene as well as a full-length recombinant tomato acidic leucine aminopeptidase gene.

This invention also relates to recombinant cells containing the recombinant nucleic acid sequence that hybridizes to a sequence that encodes a tomato acidic leucine aminopeptidase promoter. The invention further comprises cells containing heterologous nucleic acids, the expression of which is directed by the acidic leucine aminopeptidase promoter. In addition to cells containing the recombinant nucleic acid sequences, this invention encompasses transgenic plants which contain the recombinant nucleic acid sequences that hybridize to the promoter of this invention.

Methods of expressing nucleic acids in plants in response to wounding or other environmental stimuli and methods for screening proteins and other biochemicals that enhance survival in plants upon wounding or other environmental stimuli are also provided by this invention. In a preferred embodiment, a transgenic plant comprising an expression cassette having a LapA promoter of the invention operably linked to a heterologous nucleic acid which encodes a protein subject to screening is subjected to injury, and the survival of the plant is compared to the survival of a non-transgenic plant injured in the same manner.

Definitions

A "full-length genomic tomato acidic leucine aminopeptidase gene" encodes all of the coding and regulatory regions of the tomato acidic aminopeptidase gene necessary to provide expression of the full-length polypeptide in a tomato. For example, a full-length recombinant gene has all of the sequences necessary to rescue normal expression of a LapA null strain of tomato.

"Heterologous" nucleic acids are nucleic acids which are derived from different genes, or, if from the same gene, are each substantially modified.

The term "injury" in this context refers to harm or damage done to organs and/or tissues of the plant, including the roots, stems, leaves, buds, etc. The cause of injury can be mechanical, e.g., cutting, scraping, freezing, pinching, etc., or chemical, e.g., exposure of the plant to herbicides, fungicides, insecticides or lack of water, or pathogenic, e.g., infestation by bacteria, virus, fungus, etc., or by insect infestation, e.g., chewing of plant organs and/or tissues by adult insects and/or insect larvae.

The term "nucleic acid" refers to a deoxyribonucleotide (DNA) or ribonucleotide (RNA) polymer in either single- or double-stranded form, and unless otherwise limited, encompasses known analogues of natural nucleotides that hybridize to nucleic acids in a manner similar to naturally occurring nucleotides.

The phrase "operably linked" refers to functional linkage between a promoter and a second sequence, wherein the promoter sequence initiates transcription of RNA corresponding to the second sequence.

The phrase "peptides that signal flowering" refers to plant proteinaceous hormones that when present in the plant, initiate the bud formation and eventual flowering by the plant.

The phrase "peptides that initiate sap production" refers to plant proteinaceous hormones that when present in the plant, initiate the sequence that ends with the formation of sap (or syrup).

The term "plant" includes whole plants, plant organs (e.g., leaves, stems, flowers, roots, etc.), seeds and plant cells and progeny of same. The class of plants which can be used in the method of the invention is as broad as the class of higher plants amenable to transformation techniques, including both monocotyledonous and dicotyledonous plants, as well as certain lower plants such as algae. It includes plants of a variety of ploidy levels, including polyploid, diploid and haploid.

The term "promoter" refers to a region of nucleic acid subsequences located upstream and/or downstream from the start of transcription which aid in the recognition, binding and/or initiation of RNA polymerase or other transcription proteins which initiate transcription of an associated gene. A "plant promoter" is a promoter capable of initiating transcription in plant cells. A "plant leucine aminopeptidase promoter" is a promoter derived from a leucine aminopeptidase gene, e.g., by cloning, isolating or recombinantly modifying a native promoter from a leucine aminopeptidase gene.

A "recombinant nucleic acid" comprises or is encoded by one or more nucleic acid which is derived from a nucleic acid which was artificially constructed. For example, the nucleic acid can comprise or be encoded by a cloned nucleic acid formed by joining heterologous nucleic acids as taught, e.g., in Berger and Kimmel, *Guide to Molecular Cloning Techniques*, METHODS IN ENZYMOLOGY Vol. 152 Academic Press, Inc., San Diego, Calif. (Berger) and in Sambrook et al. MOLECULAR CLONING—A LABORATORY MANUAL (2nd ed.) Vol. 1–3 (1989) (Sambrook) and in CURRENT PROTOCOLS IN MOLECULAR BIOLOGY, Ausubel, F. M., et al., eds., Greene Publishing Associates, Inc. and John Wiley & Sons, Inc., (1996 Supplement) (Ausubel). Alternatively, the nucleic acid can be synthesized chemically.

A "tomato acidic leucine aminopeptidase promoter" refers to a native promoter from a tomato acidic leucine aminopeptidase gene. This promoter is optionally recombinantly fused to heterologous nucleic acids.

The phrase "wound-induced polypeptide" refers to a peptide or protein that the plant cells synthesize in response to injury to the plant.

DETAILED DESCRIPTION OF THE INVENTION

Many plants of commercial value have very specific requirements for growth and productivity. In many cases, these requirements are not economically optimal. In these plants, a transgene comprising the LapA promoter, and further encoding either LAPA proteins or other proteins or nucleic acids (e.g., antisense sequences) which are expressed in response to stress, enhances survival of the plant after wounding or other environmental stimuli. This provides transgenic plants which resist drought, pathogen infestation, salinity and alkalinity in the soil, extremes of cold and mechanical shearing during harvest.

Previous studies characterized expression of the wound-induced tomato LapA mRNAs using a cDNA clone (pDR57) (Pautot, V., et al., Proc. Natl. Acad. Sci. USA 90:9906 (1993). One of the discoveries of this invention is that the clone is a partial cDNA sequence. The full sequence of LapA1 cDNA is given as SEQ ID NO:2

In addition to overexpression of proteins and nucleic acids to enhance survival of the plant, a heterologous nucleic acid encoding a toxic factor operably linked to a LapA promoter, is introduced into cells of a plant. To kill the plant, the plant is mechanically injured, or otherwise subjected to conditions that activate the LapA promoter, causing expression of the toxic factor and death of the plant.

Previous studies characterized expression of the wound-induced tomato LapA mRNAs using a partial cDNA clone (pDR57) (Pautot, V., et al., Proc. Natl. Acad. Sci. USA 90:9906 (1993).

In one embodiment, the LapA promoter is fused to heterologous nucleic acid sequences that encodes a protein or nucleic acid that causes the transgenic plant, after stimulation by environmental changes, to flower, go dormant, or exhibit other desired characteristics.

Accordingly, the invention provides, inter alia, for transgenic nucleic acids, transgenic cells, transgenic plants, methods of modulating the survival of plants in response to environmental conditions, methods of finding genes which modulate the survival of plants, and the like.

Making Heterologous Nucleic Acids

In one class of embodiments, a LapA or other promoter of the invention is recombinantly fused to a heterologous nucleic acid. Methods of recombinantly joining nucleic acids, including cloning, in vitro ligation, and the like, are well known. Examples of appropriate recombinant techniques, including restriction enzyme digestion, ligation of nucleic acids, cloning, sequencing and the like, sufficient to direct persons of skill are found, inter alia, in Berger and Kimmel;

Sambrook et al.; and Ausubel et al.(all, supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wiss.), Glen Research, Inc., GIBCO BRL Life Technologies, Inc. (Gaithersberg, Md.), Fluka Chemica-Biochemika Analytika (Fluka Chemie AG, Buchs, Switzerland), Applied Biosystems (Foster City, Calif.), and Qiagen (Chatsworth, Calif.) as well as many other commercial sources known to one of skill.

The nucleic acid compositions of this invention, whether RNA, cDNA, genomic DNA, or a hybrid of the various combinations, are isolated from natural sources or synthesized in vitro. The nucleic acids are present in transformed or transfected whole cells, in transformed or transfected cell lysates, or in a partially purified or substantially pure form.

In vitro amplification techniques suitable for amplifying nucleic acids for use as molecular probes or generating nucleic acid fragments for subsequent subcloning are well known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as U.S. Pat. No. 4,683,202; PCR PROTOCOLS A GUIDE TO METHODS AND APPLICATIONS, Innis et al. eds., Academic Press Inc. San Diego, Calif. (1990) (Innis); Arnheim & Levinson (Oct. 1, 1990) C&EN 36–47; Kwoh, et al., Proc. Natl. Acad. Sci. USA 86:1173 (1989); Guatelli, et al., Proc. Natl. Acad. Sci. USA 87:1874 (1990); Lomell, et al., J. Clin. Chem 35:1826 (1989); Landegren, et al., Science 241:1077 (1988); Van Brunt, Biotechnology 8:,291 (1990); Wu & Wallace, Gene 4:560 (1989); Barringer, et al.Gene 89:17 (1990) and Sooknanan & Malek, Biotechnology 13:563 (1995). Improved methods of cloning in vitro amplified nucleic acids are described in U.S. Pat. No. 5,426,039.

Oligonucleotides for use as probes, e.g., in in vitro amplification methods and for use as gene probes are typically synthesized chemically according to the solid phase phosphoramidite triester method described by Beaucage & Caruthers, Tetrahedron Lett. 22:1859–1862 (1981).

Hybridization of Nucleic Acids

Single stranded forms of a nucleic acid of the invention encoding LapA promoters hybridize to the exemplar tomato LapA promoter in the sequence listing herein. Two single-stranded nucleic acids "hybridize" when they form a double-stranded stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An overview to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, Part I, Chapter 2 "Overview Of Principles Of Hybridization And The Strategy Of Nucleic Acid Probe Assays," Elsevier, New York (1993).

"Stringent conditions" in the context of nucleic acid hybridization are sequence dependent and are different under different environmental parameters. An extensive guide to the hybridization of nucleic acids is found in Tijssen, supra. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Nucleic acids which encode polypeptides and do not hybridize to each other under stringent conditions are still substantially identical if the polypeptides which they encode are substantially identical. This occurs, e.g., when a copy of a nucleic acid is created using the maximum codon degeneracy permitted by the genetic code.

An example of stringent hybridization conditions for hybridization of complementary nucleic acids which have more than 100 complementary residues on a filter in a Southern or northern blot is 50% formamide with heparin at 42° C., the hybridization being carried out overnight. An example of stringent wash conditions is a 0.2× SSC wash at 65° C. for 15 minutes (see, Sambrook, supra for a description of SSC buffer). Often the high stringency wash is preceded by a low stringency wash to remove background probe signal. An example low stringency wash is 2× SSC at 40° C. for 15 minutes for a probe with at least about 100 complementary nucleic acids.

In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithms. See, e.g., Meyers & Miller, *Computer Applic. Biol. Sci.*, 4:11 (1988); Smith & Waterman, *Adv. Appl. Math.* 2:482 (1981); Needleman & Wunsch, *J. Mol. Biol.* 48:443 (1970); Pearson & Lipman, *Proc. Nat'l. Acad. Sci. USA* 85:2444 (1988); Higgins & Sharp, *Gene* 73:237 (1988); Higgins & Sharp, *CABIOS* 5:151 (1989); Corpet, et al., *Nuc. Acids Res.* 16:10881 (1988); Huang, et al., *Computer Applications in the Biosciences* 8:155 (1992) and Pearson, et al, Methods in Molec. Biol. 24:307 (1994). Alignment is also often performed by inspection and manual alignment.

Making Conservative Modifications of Exemplar Nucleic Acids and Polypeptides

The present invention provides tomato LAP-A proteins, and conservative modifications thereof. In particular, LAP-A proteins comprising the amino terminal region of the full-length protein are provided. See also, Gu et al., *J. Biol. Chem.* 271(24):25880 (1996). The amino acids encoding the N-terminus of the protein, i.e., amino acids 1–102 were not previously known. Similarly, nucleic acids encoding this region were not available. Accordingly, in one embodiment, the present invention provides proteins (and nucleic acids encoding the proteins) which include this region. In a preferred embodiment, the protein is the full-length LAP-A protein. However, the N-terminal region is optionally fused to heterologous sequences to confer LAP-A characteristics to the heterologous sequence.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, COG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a finctionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

As described herein, sequences are preferably optimized for expression in a particular host cell used to produce the protein (e.g, a plant cell such as a tomato, or a cloning and expression system such as a yeast cell). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention.

One of skill will recognize many ways of generating alterations in a given nucleic acid sequence, which optionally provides alterations to an encoded protein. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman & Smith, *Gene* 8:81 (1979); Roberts, et al., *Nature* 328:731 (1987) and Sambrook, Innis, Ausubel, Berger, and Mullis (supra).

Most commonly, amino acid sequences are altered by altering the corresponding nucleic acid sequence and expressing the polypeptide. However, polypeptide sequences are also optionally generated synthetically on commercially available peptide synthesizers to produce any desired polypeptide (see, Merrifield, *Science* 232:341–347 (1986), Barany & Merrifield, THE PEPTIDES, Gross & Meienhofer, eds., Academic Press, N.Y., pp. 1–284 (1979); and Stewart & Young, SOLID PHASE PEPTIDE SYNTHESIS, 2d Ed., Pierce Chemical Co., Rockford, Ill., (1984).

Moreover, general knowledge regarding the nature of proteins and nucleic acids allows one of skill to select appropriate sequences with activity similar or equivalent to the nucleic acids, vectors and polypeptides disclosed herein. Exemplar conservative amino acid substitutions are described, supra.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Making Heterologous Constructs Having LapA Promoters

As described supra, the invention provides recombinant nucleic acids comprising LapA promoters operably linked to heterologous nucleic acids. The promoters and heterologous nucleic acids are operably linked using recombinant techniques, as described supra. A wide variety of heterologous nucleic acids are appropriate for operable linkage to a LapA promoter. In general, expression of the heterologous nucleic acid under the control of the promoter will either increase or decrease the survival of a plant in response to an environmental stimulus. Increasing plant survival is useful in agriculture to make recombinant plants hardier, and to serve as a selectable marker. Decreasing survival in response to environmental stimuli is also a useful selectable marker. Two general types of expressed nucleic acids which are contemplated include active RNAs such as antisense or ribozyme sequences, and RNAs encoding polypeptides.

The first type of expressed nucleic acid is an RNA with antisense or catalytic activity (e.g., a ribozyme) which blocks translation of an mRNA such as a cellular mRNA. Blocking the translation of a selected cellular mRNA modulates the survival of a plant in response to an environmental stimulus. Antisense RNA inhibition of gene expression has been shown; see, e.g., Sheehy, et al., *Proc. Nat'l. Acad. Sci. USA* 85:8805 (1988), and U.S. Pat. No. 4,801,340. In addition to antisense suppression, sense suppression of genes is also used to inhibit mRNA expression. For examples of the use of sense suppression to modulate expression of endogenous genes see, Napoli, et al., *The Plant Cell* 2:279 (1990) and U.S. Pat. No. 5,034,323.

Catalytic RNA molecules or ribozymes can also be used to inhibit gene expression. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true nucleic acid enzyme. The inclusion of ribozyme sequences within antisense RNAs confers RNA-cleaving activity upon them, thereby increasing the activity of the constructs.

A number of classes of ribozymes have been identified, and many exemplar ribozymes are available. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto, et al., *Advances in Pharmacology* 25:289 (1994) and the references therein provides an overview of ribozymes in general, including group I ribozymes, hammerhead ribozymes, hairpin ribozymes, RNAse P, and axhead ribozymes. See also, Haseloff, et al., *Nature* 334:585 (1988). Examples of GUA cleaving ribozyme genes based on the negative strand satellite RNA of the Arabis Mosaic Virus are described in De Young, et al., *Biochemistry* 34:15785 (1995).

Targets for ribozymes include mRNAs encoded by pesticide or disease resistance genes, cold resistance genes, heat resistance genes, wound-response genes and the like. By blocking the translation of these genes in transgenic plants, it is possible to make the plant susceptible to pesticides, insects, heat, cold, mechanical shearing or the like. This is useful, e.g., as a method of controlling the growth of the transgenic plants, e.g., as a negative selectable marker for the plant.

In addition to serving as a negative selectable marker, ribozymes induced in response to pathogen infection (particularly viral infection) can block replication of the virus in cells of the plant. Typically, a ribozyme engineered to cleave a pathogenic RNA needed for growth, survival, or replication of the pathogen is expressed under the control of a promoter of the invention, in a transgenic plant comprising an expression cassette under the control of the promoter. This serves to make the plant resistant to the pathogen.

The second class of nucleic acids which are desirably expressed encode proteins which improve the ability of the plant to survive stress including antimicrobial compounds such as the phytoalexins, lytic enzymes such as chitinases and glucanases, and proteinase inhibitors such as proteinaceous protease inhibitors I and II (Hildmann, et al., *The Plant Cell* 4:1157 (1992). Plants, when undergoing environmental stress, can be induced by the promoters of this invention to synthesize a variety of proteins in response to that stress. These proteins can be autologous, heterologous but still derived from plants, or from organisms other than plants, for example animals, bacteria, or fungi.

In response to pathogenic attack, some of the stress-induced proteins that are desirably induced include the lytic enzymes, such as rice chitinase (see, U.S. Pat. No. 5,530, 187) to inhibit fungal infections. To resist insect infestations, the plants are optionally engineered to express *Bacillus thuringiensis* δ-endotoxin (see Vacek, et al., *Nature* 232:732 (1986)). Abel, et al. in *Science* 232:738 (1986) found that transgenic tobacco plants expressing the coat protein of tobacco mosaic virus successfully resisted attack by the virus. Similarly, other viral coat proteins can be expressed under the control of the promoters of the invention to prevent viral infection. U.S. Pat. No. 5,614,395 describes a family of small pathogenesis related proteins that are expressed by plants undergoing a pathogenic injury. Any of these pathogenesis related proteins are optionally expressed in conjunction with a promoter of the invention.

Similar to animals, plants express heat shock proteins (hsp) in response to significant rises in temperature. These hsp include hsp70, Gmhsp17.5 from soybean (Gurley, et al., *Mol. Cell. Biol.* 6:559 (1986)) and ubiquitin (U.S. Pat. No. 5,614,399). Ubiquitin has also been found to protect plants in soil of increased metal concentrations. Any of these proteins are desirably expressed from a promoter of the invention.

In response to cold temperatures, Anderson, et al. in *Plant Physiol* 105:331 (1994) found that corn plants synthesize at least two chilling acclimation response proteins (car30 and car757). These proteins are expressed by the plants of this invention when placed under temperature stress, i.e., when the plants comprise a recombinant expression cassette under the control of the LapA promoter.

To confer resistance to herbicides, the transgenic plants of the invention are optionally engineered to express acetohydroxy acid synthase, which has been found to provide plants which overexpress this enzyme resistance to multiple types of herbicides (see, Hattori, J., et al., *Mol Gen. Genet.* 246(4):419 (1995). Other proteins that have been found to confer resistance to herbicides include: a chimeric proteins of rat cytochrome p4507A1 and yeast NADPH-cytochrome P450 oxidoreductase (Shiota, et al., *Plant Physiol.* 106(1)17 (1994) and phosphotransferases (Datta, et al., *Plant Mol. Biol.* 20(4):619 (1992). Glutathione reductase and superoxide dismutase (Aono, et al., *Plant Cell Physiol.* 36(8):1687 (1995), have been found to confer resistance to fungal toxins and oxidative stress in cold, salinity, drought and wounding.

U.S. Pat. No. 5,614,395 describes transgenic plants which express malate synthetase and a amylase isozymes in response to chemically induced injury similar to the ABA and MeJa injuries described in this invention.

Finally, under anaerobic conditions, transgenic plants are optionally induced to express high levels of alcohol dehydrogenase (see also, U.S. Pat. No. 5,614,395).

Making Transgenic Plants

The DNA constructs of the invention may be introduced into plant cells, either in culture or in organs of a plant, e.g., leaves, stems, fruit, etc. The expression of natural or synthetic nucleic acids can be achieved by operably linking a nucleic acid of interest to the LapA promoter, incorporating the construct into an expression vector, and introducing the vector into a suitable host cell.

Typical vectors contain transcription and translation terminators, transcription and translation initiation sequences, and promoters useful for regulation of the expression of the particular nucleic acid, i.e., LapA. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Berger & Kimmel; Sambrook and Ausubel.

Cloning of LapA Promoters into Bacterial Hosts

Bacterial cells can be used to increase the number of plasmids containing the DNA constructs of this invention. The bacteria can be grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAexpress Expression System, Qiagen). The isolated and purified plasmids can then be further manipulated to produce other plasmids, used to transfect plant cells or incorporated into *Agrobacterium tumefaciens* to infect plants.

There are several well-known methods of introducing nucleic acids into bacterial cells, any of which may be used in the present invention. These include: fusion of the recipient cells with bacterial protoplasts containing the DNA, electroporation, projectile bombardment, and infection with viral vectors, etc.

The in vitro delivery of nucleic acids into bacterial hosts can be to any cell grown in culture. Contact between the cells and the genetically engineered nucleic acid constructs, when carried out in vitro, takes place in a biologically compatible medium. The concentration of nucleic acid varies widely depending on the particular application, but is generally between about 1 $\mu$M and about 10 mM. Treatment of the cells with the nucleic acid is generally carried out at physiological temperatures (about 37° C.) for periods of time of from about 1 to 48 hours, preferably of from about 2 to 4 hours.

Alternatively, the nucleic acid operably linked to the LapA promoter to form a fusion gene can be expressed in bacteria such as *E. coli* and its gene product isolated and purified. Introduction of the LapA promoter sequence may be accomplished by the methods described above. See also, Polak J. & Novick, R. P., *Plasmid* 7:152 (1982).

Transfecting Plant Cells

The DNA constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence fimctions of the *Agrobacterium tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are also well described in the scientific literature. See, for example Horsch, et al., *Science* 233:496–498 (1984), and Fraley, et al., *Proc. Nat'l. Acad. Sci. USA* 80:4803 (1983). Agrobacterium-mediated transformation is a preferred method of transformation of dicots.

Generation of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, (1983); and Binding, REGENERATION OF PLANTS, PLANT PROTOPLASTS, pp. 21–73, CRC Press, Boca Raton, (1985). Regeneration can also be obtained from plant callus, explants, somatic embryos (Dandekar, et al., *J. Tissue Cult. Meth.* 12:145 (1989); McGranahan, et al., *Plant Cell Rep.* 8:512 (1990)), organs, or parts thereof. Such regeneration techniques are described generally in Klee, et al., *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Avena, Brassica, Citrus, Citrullus, Capsicum, Cucumis, Cucurbita, Daucus, Fragaria, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea. The LapA genes of the invention are particularly useful in the production of transgenic plants in the genus Lycopersicon and Brassica.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Discussion of the Accompanying Sequence Listing

SEQ ID NO:1 provides the sequence of the LapA1 promoter region. SEQ ID NO:2 provides the LapAl cDNA coding sequence. SEQ ID NO:3 provides the sequence of the LapA2 promoter region. SEQ ID NO:4 provides the coding cDNA sequence of LapA2. In each sequence, the information is presented as a DNA sequence. One of skill will readily understand that the sequences also fully describes corresponding RNA (i.e., by substitution of the T residues with U residues) complementary strands of the given sequences and a variety of conservatively modified variations of the DNA and RNA sequences. In addition, coding nucleic acid sequences provide the corresponding amino acid sequence by translating the given DNA sequence using the genetic code.

SEQ ID NO:5 provides the protein sequence of the full-length LapA1 protein from tomato. SEQ ID NO:6 is a partial protein sequence of LapA2 from tomato. The cDNA from which this sequence was derived was incomplete at the 5' end and the first 6 amino acids are missing from the amino acid sequence. From SEQ ID NO:5, the N-terminal amino acids are believed to be MATLRV (SEQ ID NO:7). SEQ ID NO:6 contains 3 amino acid substitutions compared to SEQ ID NO:5. The information presented in SEQ ID NO:5 and 6 is presented as polypeptide sequences. One of skill will readily understand that the sequences also describe all of the corresponding RNA and DNA sequences which encode the protein, by conversion of the amino acid sequence into the corresponding nucleotide sequence using the genetic code, ie., by alternately assigning each possible codon in each possible codon position. The sequence also provides a variety of conservatively modified variations by substituting appropriate residues with the exemplar conservative amino acid substitutions provided, as described above.

Measuring Lap A Promoter Activity

LapA promoter activity can be determined by measuring the difference upon wounding or other selected environmental stimuli including, drought, freezing, etc., in mRNA transcribed by genes under the control of the LapA promoter. Alternatively, the level of protein produced from this transcribed RNA. can be determined before and after wounding.

For example, promoter activity can be measured in a quantitative northern blot which directly measures the amount of RNA in a selected biological sample which is transcribed from a gene regulated by the promoter. Performing quantitative northern blot analysis is ubiquitous in the art, with information sufficient to guide one of skill being found in Ausubel, Berger, and Sambrook, all supra. In brief, RNA is isolated from a selected biological sample (e.g., plant tissue from a recombinant plant comprising a heterologous nucleic acid under the control of a LapA promoter which has been mechanically wounded), with a selected aliquot of the RNA being run through an electrophoretic gel, and blotted onto a suitable membrane. The membrane is then probed with a labeled probe specific for the heterologous nucleic acid. The level of probe hybridization is quantified, e.g., by densitometric measurement of an autoradiograph film exposed to the filter.

Similarly, the level of RNA can be measured indirectly using quantitative PCR. This procedure is also common in the art, with information sufficient to guide one of skill found in Innis, Ausbuel, Berger, and Sambrook, all supra. In brief, RNA is isolated from the biological sample in question (e.g., using a poly $A^+$ affinity procedure which selectively isolated mRNA), followed by reverse transcription of the RNA and quantitative PCR amplification. In another indirect method, catalytically active RNA levels (e.g., where the gene encodes a transcribed RNA ribozyme) can be measured by measuring the activity of the active RNA. For example, cleavage of a target RNA by an encoded ribozyme can be monitored (e.g., by northern blot, or quantitative PCR). The level of cleavage correlates to the amount of catalytically active ribozyme in a selected sample.

In addition to measuring RNA levels, the level of protein encoded by an RNA can also be measured. Typically, this is suitably performed for proteins which are not translationally regulated, so that the level of protein corresponds to the amount of RNA which is transcribed from a gene under the control of a promoter. Protein determinations are routine in the art, commonly being performed by western blot analysis, ELISA or other affinity detection techniques which monitor the level of protein in a sample. See, Coligan, CURRENT PROTOCOLS IN IMMUNOLOGY, Wiley/Greene, N.Y. (1991); and Harlow & Lane, ANTIBODIES: A LABORATORY MANUAL, Cold Spring Harbor Press, N.Y. (1989). See also, Ausubel, supra.

The level of induction of a promoter by an environmental stimulus refers to the percent or fold increase in the production of transcribed or translated gene products under the control of a promoter in response to a stimulus. Preferred LapA promoters in transgenic plants comprising the promoters are induced at least about 5- fold, generally at least about 10-fold, often at least about 50-fold, and preferably at least about 100-fold in response to mechanical wounding of the plant, in the mechanically wounded tissues. In one preferred embodiment, the tomato LapA promoter shows a 130- fold increase in activity following mechanical wounding. Measurement of induction is performed by measuring the level of promoter activity before application of the environmental stimulus and measuring the level of activity after the environmental stimulus and comparing the two levels of activity.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLE 1

Localization and Post-translational Processing of LapA in Tomato

Previous studies characterized expression of the wound-induced tomato LapA mRNAs using a partial cDNA clone (pDR57) (Pautot, V., et al., Proc. Natl. Acad. Sci. USA 90:9906 (1993). In this Example, mRNAs are more completely characterized by full length cDNA clones and the mRNAs correlated with the LapA1 and LapA2 genes in the tomato genome.

The deduced amino acid sequence from the tomato LapA cDNAs suggests that LAPA is synthesized as a precursor protein. This is supported by in vitro transcription and translation of a full-length LapA1 cDNA. The in vivo processing of preLAPA into mature LAPA is demonstrated by expression of full-length LapA1 cDNA in insect cells using a baculovirus expression system.

Finally, direct protein sequencing shows that the major LAPA polypeptide that accumulates in wounded leaves has two different N-termini. The LAPA presequence has features suggesting a role in targeting LAPA to the plastid; however, immunoblot analysis of chloroplast and total proteins indicate only a small fraction of the wound-induced LAPA is plastid localized.

Plant Material and RNA Isolation

*Lycopersicon esculentum* Peto238R plants were grown to the 4- to 6-leaf stage in a growth chamber. Details on plant growth conditions, methods for wounding, tissue harvest, and RNA isolation and quantitation have been described in Pautot, V., et al., *Mol. Plant-Microbe Interact.* 4:284 (1991).

Construction and Screening of a Wound-induced cDNA Library

Poly(A$^+$) mRNA was isolated from tomato leaves 24 hr after mechanical wounding. cDNAs were synthesized and packaged into gt11 Sfi I-Not I cDNA arms according to manufacturer's instructions (Promega, Madison, Wiss.). The primary library contained 1.5×10$^6$ recombinants. Approximately 10$^5$ phage from the unamplified cDNA library were screened using a partial LapA1 cDNA clone (pDR57) (Pautot, V., et al., *Proc. Nat'l. Acad. Sci. USA* 90:9066 (1993)). pDR57 was labeled with [α-$^{32}$P]-dCTP (3000 Ci/mmole; Amersham, Arlington Heights, Ill.) using the random primer method of Feinberg, A. P. and Vogelstein, B., *Anal. Biochem.* 132:6 (1983). The pre-hybridization, hybridization, and wash conditions have been described in Walling, L. L., et al., *Nuc. Acids Res.* 16:10477 (1988). LapA positive clones were plaque-purified by secondary and tertiary screenings.

Characterization of LapA cDNA Clones

Phage were eluted from individual plaques in 500 μL SM buffer (0.01% gelatin, 50 mM Tris-HCl, pH 7.5, 100 mM NaCl, 8 mM MgSO$_4$). Using the left (5'-TGGCGACGACTCTGGAGCCG-3'(5'-TGACACCAGACCAACTGGTAATGG-3'; SEQ ID NO:9); SEQ ID NO:8) and right λgt11 primers and 10 μL of phage eluate, LapA1 cDNA inserts were amplified using the polymerase chain reaction (PCR). The λgt11 primers were synthesized by the Biotechnology Instrumentation Facility (University of California, Riverside, Calif.). The temperature cycle for PCR amplification was 1 min at 94° C., 1 min at 60° C., and 3 min at 72° C. Only clones with near full-length inserts (approximately 2 kb) were further analyzed. PCR products were digested with Xba I to identify the two classes of LapA cDNAs.

λ DNAs were purified (see, Manfioletti, G. & Schneider, C., *Nuc. Acids Res.* 16:2873 (1988)) and Sfi I/Not I-digested LapA cDNA inserts were cloned into pGem11 (Promega). For DNA sequencing, LapA1 and LapA2 cDNA inserts in pGEM11 were cloned into Sma I-digested pBluescript SK (pBlapA1 and pBlapA2, respectively). DNA sequencing was facilitated by generating a series of nested deletions using exonuclease III (Henikoff, S., *Meth Enzymol.* 155:156 (1987)). The DNA sequence of both strands was determined by the dideoxy chain-termination method using Sequenase (United States Biochemical, Cleveland, Ohio) and [$^{35}$S]-dATP (>1000 Ci/mmol; Amersham). The degree of peptide similarity for the deduced LapA polypeptides and the alignments of the animal, prokaryotic and plant LAPs were determined using the GAP or PILEUP programs of the University of Wisconsin, Genetics Computer Group, respectively.

DNA Blot Hybridization

DNA blots with Xba I-digested λLap clones were hybridized with a $^{32}$P-labeled pBlapA1-3UTR probe (Feinberg, A. P. and Vogelstein, B., *Anal. Biochem.* 132:6 (1983). pBlapA1-3UTR was a Spe I/EcoR I subclone of pBlapA1 and contained only the 3'-UTR of the LapA1 cDNA. Hybridization conditions and washes were performed as described by Walling, L. L., et al., *Nuc. Acids Res.* 16:10477 (1988).

In Vitro Translation and Immunoprecipitation pBlapA1 (2 μg) was transcribed and its RNA was translated in the presence of [$^{35}$S]-methionine using the TNT™ coupled transcription-translation system from Promega. The translation mixture was directly fractionated in 12% SDS-PAGE (Wang, C. S., et al., *Plant Physiol.* 99:822 (1992)) or immunoprecipitated with the tomato LAP polyclonal antiserum (Gu, Y.-Q., et al., *Plant Physiol.* 110:1257 (1996). Immunoprecipitation of translated proteins was according to Kessler, S. W., *J. Immunol.* 115:1617 (1975) with the following modification. The translation mixture (20 μL) was diluted to 1 mL with 1× TPBS (170 mM NaCl, 6.2 mM KCl, 12.6 mM Na$_2$HPO$_4$, 2.2 mM KH$_2$PO$_4$, pH 7.4, 0.5% Triton X-100). LAP polyclonal antibodies (50 μL) were added and incubated on ice for 2 hr with gentle shaking. The antibody-antigen complexes were precipitated by adding 50 μL Immunoprecipitin (Bethesda Research Laboratories, Bethesda, Md.), incubating on ice for 1 hr, and centrifugation at 12,000 g for 2 min. The pellet was resuspended and washed three times with 1× TPBS. The protein pellet was boiled for 2 min in 2% SDS and 6 M urea. After removal of Immunoprecipitin by centrifugation at 10,000g for 2 min, SDS sample buffer was added to give a final concentration of 2.3% SDS, 5% β-mercaptoethanol, 10% glycerol, 0.05% bromophenol blue, and 62.3 mM Tris-HCl (pH 6.8). The immunoprecipitated proteins were fractionated by 12% SDS-PAGE (Wang, C. S., et al., *Plant Physiol.* 99:822 (1992)).

Expression of the LapA1 cDNA in Insect Cells

A LapA1 cDNA lacking the LapA1 5'-UTR was ligated into the baculovirus polyhedrin expression vector, pV1393 (In Vitrogen, San Diego, Calif.) that had been digested with BamH I and Sma I. The resulting plasmid, pVlap1ATG, fused the baculovirus polyhedrin promoter and its 5'-UTR with the complete coding region and 3'-UTR of LapA1. Site-directed mutagenesis of the LapAl insert in pBlapA1 was necessary to create a BamH I site and to minimize the number of nucleotides added to the polyhedron promoter-directed transcript. These gene manipulations have been detailed in Gu, Y.-Q., Ph.D. Thesis, University of California, Riverside, Calif. (1994).

Trichoplusiani TN5 cells were propagated in monolayer cultures and *Autographa californica* nuclear polyhedrosis virus (AcMNPV) infections were performed as described by Summers, M. D. & Smith, G. E., A MANUAL OF METHODS FOR BACULOVIRUS VECTORS AND INSECT CELL CULTURE PROCEDURES, Texas Agricultural Experiment Station Bulletin No. 1555 (1985). TN5 cells ($2\times 10^6$ cells) were cotransfected with 0.5 μg of linearized AcMNPV virus (PharMigen, San Diego, Calif.), 3 g pVlap1ATG and 5 μL of liposomes (Bethesda Research Laboratories). Five days later, the media from the transfected cells were screened for recombinant virus (AcMNPV-lapA1) by infecting TN5 cells in a 96-well plate with serial dilutions of the transfection media. Media from recombinant-positive wells were used for several rounds of infection of TN5 cells to produce a high titer recombinant virus. For LAP expression studies, TN5 cells were plated at $2.5-10^6$ cells/60-mm culture dish and were infected with $3\times 10^5$ pfu of either wild-type AcMNPV or AcMNPV-lapA1. Cells were harvested every day for 6 days after infection.

Methyl Jasmonate Treatment and Isolation of Chloroplasts

A 500 mM methyl jasmonate (MeJa)/90% ethanol stock was used directly or diluted in water prior to use. One-month-old tomato plants were excised at the base of the stem. Excised plants were placed in a flask with 250 mL of 10 μM MeJa/0.002% ethanol in an air-tight glass desiccator. The desiccator contained a cotton-tipped applicator that had been wetted with 1 μL of 500 mM MeJa/90% ethanol. Excised plants incubated in 250 mL of 0.002% ethanol in a desiccator with a cotton-tipped applicator wetted with 1 μL of 100% ethanol served as controls. MeJa-treated and control plants were incubated for 24 hr prior to tissue harvest. Chloroplasts were isolated using the method described in Chao, W. S., et al., *Plant Physiol.* 107:253 (1995) and total proteins were extracted. Integrity of plastids were confirmed by light microscopy.

Extraction, Fractionation and Immunoblot Analysis of Proteins

Extraction of soluble and insoluble proteins in TN5 cells was according to MacDonald, P. N., et al., *J. Biol. Chem.* 266:188808 (1991); total proteins from insect cells, wounded and MeJA-treated tomato leaves, and chloroplasts from MeJA-treated leaves were extracted as described by Wang, C. S., et al., *Plant Physiol.* 99:822 (1992)). Proteins were dissolved in the solubilization buffer for 2D-PAGE (Hurkman, W. J. & Tanaka, C. K., *Plant Physiol.* 81:802 (1986)).

For extraction of leaf soluble proteins, 15 g of wounded tomato leaves were harvested and homogenized with a blender in 30 mL of extraction buffer (50 mM Tris-HCl, pH 6.8, 1% β-mercaptoethanol, and 5% insoluble polyvinylpyrolidone). The homogenate was filtered through three layers of miracloth and centrifuged at 100,000 g for 60 min at 4° C. to remove organelles and membranes. Soluble proteins were precipitated by adding 5 vol of cold acetone and stored at −20° C. for 16 hr. After centrifugation, the protein pellet was washed twice with cold acetone (−20° C). The final pellet was dried under vacuum for 1 min and resuspended in the solubilization buffer for 2D-PAGE.

SDS- and 2D-PAGE were performed as described in Wang, C. S., et al., *Plant Physiol.* 99:822 (1992)). After electrophoresis, the gels were stained with Coomassie Blue R-250 or electrophoretically transferred to nitrocellulose filters (0.48 μm, Schleicher and Schuell BA85). The pIs of polypeptides were determined as described previously (Gu, Y.-Q., et al., *Plant Physiol.* 110:1257 (1996)). The immunoblot analyses were carried out according to Gu, et al. (id.) using a 1:500 dilution of the polyclonal antibodies made against the LAP-A1 protein of tomato.

Determination of the N-terminal Amino Acid Residues of the Major LAP-A Protein Soluble proteins from wounded leaves were fractionated by 2D-PAGE, electrotransferred to ProBlot™ membrane (Applied Biosystems) in cold 1× CAPS transfer buffer (10 mM 3-[cyclohexylamino]-1-propanesulfonic acid, 10% methanol, pH 11.0). The transfer was performed at constant voltage (50 V) for 40 min at room temperature. The membrane was rinsed several times in Milli-Q $H_2O$, saturated in methanol for 5 sec, stained with 0.1% Coomassie Blue R-250/40% methanol/0.5% acetic acid for 20 sec, and destained by rinsing three times in 50% methanol for 2 min/wash. The major LAP-A polypeptide was excised from the membrane with a razor blade. The UC Riverside Biotechnology Instrumentation Facility analyzed six residues from the N-terminus of the major LAP-A polypeptide using an Applied Biosystem sequenator.

Isolation of Full-length cDNAs Encoding the Tomato Wound-induced LAP

To isolate full-length LapA cDNAs, a λgt11 Sfi I/Not I cDNA library was constructed from mRNA isolated from wounded leaves of tomato and screened using a partial LapA1 cDNA clone, pDR57. Two classes of λlap cDNA clones were distinguished by the presence or absence of an Xba I site. The LapA1 and LapA2 cDNA clones chosen for study had the longest cDNA inserts identified. The complete λlapA1 cDNA clone (pBlapA1) lacked an Xba I site and had a 1930-bp insert. Based on results from RNase protection assays (see, infra) and the size of the LapA mRNA (2.0 kb) as determined in Pautot, V., et al., *Proc. Nat'l. Acad. Sci. USA* 90:9906 (1993), the LapA1 sequence presented here was determined to be full-length. The cDNA had a short 5'-UTR (18 bp) that was followed by a large open reading frame encoding a 571 amino acid residue protein. This protein had a molecular mass of 60 kDa which is 5 kDa larger than the mature LAP-A protein (Gu, Y.-Q., et al., *Plant Physiol.* 110:1257 (1996)). The context of the translation start site (UACA<u>AUG</u>GC) fitted the translational consensus sequence (AACA<u>AUG</u>GC) of Gallie, D. R., *Annu. Rev. Plant Physiol. Mol. Biol.* 44:77 (1989)). Four putative polyadenylation signals (AAUAAA) were noted within the 170-bp 3'-UTR of LapA1.

LapA2 cDNA clones with Xba I sites were also characterized. Only six nucleotide substitutions (at positions 1090, 1558, 1561, 1562, 1617, and 1647) were noted in the LapA1 and LapA2 coding regions. Two changes resulted in amino acid substitutions; the Arg-358 in LapA1 was a Gly in LapA2 and the LapA1 Thr-515 was changed to Leu in LapA2. The 3'-UTRs of LapA1 and LapA2 were more divergent, although still highly conserved in sequence (93% identity). Nine nucleotide substitutions were observed in 170 bp of the LapA1 3'-UTR. One substitution created the Xba I site in 3'-UTR of LapA2. The LapA1 and LapA2 cDNAs had different sized 3'-UTRs which may have resulted from utilization of different polyadenylation signals.

Genomic DNA blot analysis (Pautot, V., et al., *Proc. Nat'l. Acad. Sci. USA* 90:9906 (1993)) and analysis of λlap genomic clones indicated that there are two tightly linked genes encoding the wound-induced LAP-A in tomato. DNA blot analysis of Xba I-digested λlap genomic clones and a 3'-UTR probe indicated that the LapA1 and LapA2 cDNA clones are encoded by different genes and do not represent alleles of one LapA gene (Gu, Y.-Q., Ph.D. Thesis, University of California, Riverside, Calif. (1994)).

In vitro Translation of a Full-length LapA1 cDNA

Using polyclonal antibodies to the wound-induced LAP-A of tomato, four classes of LAP and LAP-like proteins in tomato plants were identified (Gu, Y.-Q., et al., *Plant Physiol.* 110:1257 (1996)). Only the acidic, 55-kDa LAP-As were wound-induced. The first translation initiation codon (nucleotide 19) identified a large open reading frame encoding a 60-kDa LAP-A protein with a pI of 6.3. A second potential initiation codon was located 291 nucleotides downstream and if this ATG was utilized, a protein of 50 kDa would be synthesized. While this AUG was not in a nucleotide context (UGAC<u>AUG</u>GC) that favored efficient translation in plants (Gallie, D. R. *Annu. Rev. Plant Physiol. Mol. Biol.* 40:471 (1989)) and the deduced polypeptide was 5 kDa smaller than the observed size of the mature LAP-A from wounded leaves as determined by SDS-PAGE (Gu, Y.-Q., et aL, *Plant Physiol.* 110:1257 (1996)), the pI (5.5) of this protein was close to that observed for the mature LAP-As from wounded leaves (Gu, et al., id.) Therefore, it was essential to determine which translational start codon was utilized.

To discriminate between the alternative initiation sites at nucleotide positions 19 and 301, the LAP-A1 protein was synthesized in vitro using the pBlapA1 plasmid and an in vitro coupled transcription-translation system. $^{35}$S-labeled proteins were fractionated by SDS-PAGE and a prominent 60-kDa protein was detected. Immunoprecipitation of the in vitro synthesized 60-kDa protein revealed that it was a plant LAP. Taken together, these results indicated that the wound-induced LAP-A1 was synthesized as a 60-kDa precursor protein.

Processing of the LAP-A Precursor Protein in Insect Cells

To test whether the processing of the 60-kDa LAP-A precursor into the 55-kDa mature LAP-A occurred in vivo, expression of the full-length LAP-A was evaluated in *E. coli* and in insect cells. The LAP-A preprotein was not processed to its mature form in *E. coli* and accumulated to high levels in inclusion bodies. However, processing of the LAP-A preprotein was observed in TN5 cells infected with AcMNPV-lapA1 or AcMNPV and harvested at 1, 2, 3, 4, 5 and 6 days after infection. Soluble proteins and insoluble proteins were isolated and subjected to SDS-PAGE immunoblot analyses using the plant LAP-A antiserum. In the control infection with AcMNPV, no cross-reactive proteins at 60- and 55-kDa were observed in total protein extracts; a 70-kD protein had a weak immunoreaction with the LAP polyclonal antiserum. The 60-kDa LAP-A precursor protein was detected 2 days after infection in the soluble and insoluble protein fractions. On the fourth day, a processed form of LAP-A with a size of 55 kDa was detected as a soluble protein. As the infection progressed (days 5 and 6), the majority of the LAP-A precursor and mature LAP-A accumulated in the insoluble fraction.

To ensure that the 55-kDa LAP-A protein that accumulated in insect cells represented the processed LAP-A protein and not a random degradation product, proteins from infected TN5 cells were fractionated by 2D-PAGE and subjected to immunoblot analysis. The TN5 cells accumulated multiple forms of the 60-kDa LAP-A proteins with pIs ranging from 6.2–6.4. This correlated well with the pI of the precursor protein deduced from the LapA1 cDNA clone (pI=6.4). In addition, multiple forms of the mature 55-kDa protein were detected and their pIs ranged from 5.6 to 5.8. These results were consistent with our previous findings that the 55-kDa LAP-As detected in wounded tomato leaves had five forms in a pI range of 5.6 to 5.9 (Gu, Y.-Q., et al., *Plant Physiol.* 110:1257 (1996)).

Determination of the N-terminal Residues of the Mature Acidic LAP Protein

The acidic LAPs were significantly enriched in soluble protein extracts from wounded tomato leaves. The 2D-PAGE profiles of total and soluble leaf protein profiles were distinct when visualized by Coomassie Blue-staining. The 2D-immunoblot pattern of soluble proteins from wounded leaves was similar to that of phenol-extracted total leaf proteins. All four classes of LAP and LAP-like proteins were detected. In the acidic region of these 2D gels, three abundant, soluble, 55-kDa polypeptides were visualized by Coomassie Blue staining. To determine which of these polypeptides corresponded to the acidic LAP-A, the three polypeptides were excised from a 2D gel, re-fractionated by SDS-PAGE, blotted, and incubated with the LAP polyclonal antiserum. The results indicated that one of the proteins corresponded to the mature acidic LAP-A protein.

The mature LAP-A was fractionated by preparative 2D-PAGE, the major LAP-A protein was identified and subjected to N-terminal analysis (see *Materials and Methods*). Equimolar amounts of two amino acids were detected at the first five N-terminal positions and a single amino acid was detected at the sixth position. Inspection of the deduced amino acid sequence of the LapA1 and LapA2 cDNA clones revealed that these data were consistent with the presence two N-termini for the LAP protein that were present in equivalent amounts. One polypeptide began at residue 54 and had the sequence Ile-Ala-Gly-Asp-Thr-Leu (SEQ ID NO:10): the second polypeptide began with residue 56 and had the sequence Gly-Asp-Thr-Leu-Gly-Leu (SEQ ID NO:11). This predicts the 53- and 55-residue presequences were processed in vivo.

Localization of the LAP-A Proteins

While tomato and potato LAP presequences had features that were very similar to transit peptides that target proteins to the plastid (Keegstra, K. & Olsen, L., *Annu. Rev. Plant Physiol. Mol. Biol.* 40:471 (1989); Gavel, Y. & von Heigne, G., *FEBS Lett.* 261:455 (1990)), cell fractionation studies suggested that the tomato LAP-A proteins were soluble proteins (Gu, Y.-Q., et al., *Plant Physiol.* 110:1257 (1996)). To determine if tomato LAP proteins were plastid localized, chloroplast proteins and total proteins were isolated from leaves from control plants and plants that were treated with methyl jasmonate (MeJa). Jasmonic acid and MeJa are potent inducers of some wound- and defense-response genes, including LapA genes (Schaller, A., et al., *Plant Cell* 7:1893 (1995)). Tomato LAP antiserum immunoblots indicated that LAP proteins could be detected in chloroplasts from leaves of MeJa-treated plants. However, a comparison of the chloroplast and total protein extract immunoblots indicated that the majority of the tomato LAP proteins were not plastid-localized.

EXAMPLE 2

Characterization of LapA Promoters

The entire gene sequences for two tomato wound-induced leucine aminopeptidases, LapA1 and LapA2, were isolated and characterized. LapA1 and LapA2 were organized in a tandem array with approximately 6 kb separating their coding regions. Quantitation of LapA mRNA levels in conjunction with nuclei run-on experiments indicated that LapA genes were primarily under transcriptional control. In response to mechanical wounding, LapA transcription rates increased over 120-fold. DNA sequence analysis indicated that LapA1 and LapA2 5'-flanking regions were greater than 85% identical in the first 929 bp. RNase protection studies and DNA sequence data revealed that LapA1 and LapA2 had short 18-bp 5'-untranslated regions.

Plant Materials and Wounding.

Tomato plants (*Lycopersicon esculentum* 238R and *Lycopersicon esculentum* VFNT cherry) were 1 month old when processed. All plants used in this study were grown in a growth chamber in soil with a 16 h (30° C.)/8 h (20° C.) light/dark cycle, watered daily with water and supplemented with osmocote. Leaves were wounded by crushing with needle-nosed pliers and harvested 24 h later. Tomato 238R leaves were wounded twice; the second wounding was performed 18 h after first wounding, and leaves were harvested 6 h later. Leaves from 1-month-old tomato plants were used in the nuclei run-on experiments. Leaves were wounded once with pliers and were harvested 0, 4, and 24 h later; leaves were infected with Pseudomonas V., et al., *Mol. Plant-Microbe Interact.* 4:284 (1991). All leaves were excised, frozen in liquid nitrogen, and stored at −80°0 C.

Genomic Clone Isolation and Characterization.

The λLapA genomic clones were isolated by screening a tomato genomic DNA library with a leucine aminopeptidase cDNA clone, pDR57 as described in Example 1. The λCharon 35 library containing *L. esculentum* VFNT cherry partial-Sau 3A fragments was kindly provided by Dr. Robert Fisher (University of California, Berkeley, Calif.).

Preliminary restriction enzyme mapping data indicated that the genomic DNA segments in the λLapA clones did not have Sma I sites. Therefore, the inserts were subcloned into the Sma I site of pBS-SK. Restriction enzyme maps were determined by single or double restriction enzyme digestions using EcoR I, EcoR V, Sac I, BamH I, and Apa I. When needed, subclones with smaller DNA fragments were constructed to map regions with many restriction enzyme sites. The polarity of the LapA genes was determined by DNA blots analyses of LapA subclones with $^{32}$P-labeled LapA1 3'-region (pDR57) or 5'-region (pLapA1-E) probes.

RNase Protection Assays

To map 5' mRNA ends, antisense were synthesized using T3 RNA polymerase from templates (pLapA1-E and pLapA1-X) that were linearized with Xho I. pLapA1-E was a 1.8-kb EcoR I subclone of λLapA1-4 and pLapA1-X was a Xba I-EcoR I subclone of pLapA1-E. To map mRNA 3' termini, antisense RNAs were synthesized using the SP6 RNA polymerase and templates (pBLapA1-ES and pBLapA2-ES) linearized with Sfi I. The pBLapA1-ES and pBLapA2-ES subclones were described previously (Gu, Y.-Q., et al., *J. Biol Chem.* 271(24):25880 (1996)) and contained the 3'-untranslated regions of LapA1 and LapA2, respectively. In vitro synthesized RNAs (specific activity= $5 \times 10^7$ cpm/lg) were synthesized with T3 or SP6 RNA polymerases in the presence of $\alpha$-[$^{32}$P]-ATP according to manufacturer's specifications (GIBCO-BRL). Antisense RNAs were dissolved in 40 μL of hybridization buffer (40 mM PIPES (pH 6.4), 1 mM EDTA, 0.4 M NaCl, 80% formamide).

The hybridization reaction (30 μL) included 2 μL of $^{32}$P-labeled antisense RNAs ($2.5 \times 10^6$ cpm) and 2.5 μg poly(A$^+$) mRNA. RNase protection assays were performed according to the method of Sambrook. After hybridization and processing, RNAs were dissolved in 6 μL of double-distilled water, and 4 μL of USB stop solution (United States Biochemical, Cleveland, Ohio) was added. RNA samples were heated for 2 min at 75° C. and immediately cooled on ice. Samples were run on 6% polyacrylamide gels for 2 h, dried, and exposed to Hyper-film-MP (Amersham Co.) overnight.

DNA Sequencing

A 1.8-kb EcoR I/Hind III fragment containing the LapA1 5'-flanking region was subcloned (pLapA1-EH). Overlapping serial deletions of this clone were made using exonuclease III according to Henikoff, S., *Meth. Enzymol.* 155:156 (1987). The sequence of both strands was obtained by the dideoxy chain-termination method using Sequenase (United States Biochemical) and $\alpha$-[$^{35}$S]-dATP (Amersham Co.).

RNA isolation, RNA blot and dot blot analyses

Isolation of total RNAs, poly(A$^+$) mRNAs, and RNA blot hybridizations were described previously (Pautot, et al., *Mol. Plant-Microbe Interact.* 4:284 (1991)). Blots were hybridized, washed and exposed to Hyper film-MP at −80° C. with a Dupont intensifying screen for 6 h to 3 d. The probe was labeled using $\alpha$[$^{32}$P]-dCTP by nick translation according to manufacturer's specifications (GIBCO-BRL).

To quantitate LapA mRNA levels in the poly(A$^+$) mRNA pool, full-length length LapA1 mRNAs were synthesized in vitro using pBLapA1 as a template (Gu, Y.-Q., et al., *J. Biol. Chem.* 271(24):25880 (1996)). pBLapA1 was linearized with Hind III and sense-strand RNA was synthesized using T3 RNA polymerase; RNA synthesis was quantitated using a radioactive tracer. In vitro synthesized LapA mRNA and poly(A$^+$) mRNAs were serially diluted and tRNA added to bring RNAs to 1.0 μg (Chang Y. C. Walling, L. L., *Plant Mol. Biol.* 19:217 (1992)). RNAs were fractionated on 1.2% denaturing agarose gels, blotted and hybridized with a $^{32}$P-labeled pBlapA1. RNA levels were quantitated from autoradiographs in a linear exposure range using a LKB UltroScan XL laser densitometer (LKB Produkter AB; Bromma, Sweden).

To determine the magnitude of induction of LapA mRNAs after wounding, poly(A$^+$) mRNAs from healthy and wounded plants were serially diluted and supplemented with tRNA as described above. RNA slot blot hybridization was done according to Sambrook. RNA samples were denatured in 50% formamide, 6.5% formaldehyde, and 1×SSC (1×SSC=0.15 M NaCl, 0.015 M sodium citrate) at 68° C. for 15 min and loaded onto a nitrocellulose filter using a BRL slot blot apparatus. The filter was hybridized with a $^{32}$P-labeled pBLapA1. After autoradiography, slots were excised from the filter and quantitated by liquid scintillation counting (Beckman LS 1801; Beckman Instruments, Irvine, Calif.).

Total Protein Extraction, Fractionation, and Immunoblot Analyses

Total leaf proteins were extracted and fractionated by SDS-PAGE or 2D-PAGE as described by Wang, C.-S., et al., Am. J. Bot. 79:118 (1992). Electro-transfer and immunoblot procedures were described in Gu, Y.-Q., et al., Plant Physiol 110: 1257 (1996). The production of the polyclonal and LAP affinity-purified antibodies was described (Gu, et al., id.). A 1:500 dilution of the LAP polyclonal antiserum and the preimmune serum were used. LAP affinity-purified antibodies were diluted 1:20 prior to use.

Organization of LapA Genes in the Tomato Genome

To determine the number of genes encoding the wound-induced LAP proteins and their organization in the tomato genome, six different λLapA genomic clones were isolated and characterized by restriction enzyme mapping and DNA blot analyses. The organization of the 28-kb LapA genomic DNA indicated that LapA1 and LapA2 were linked and organized in a tandem array with approximately 6 kb separating the LapA1 coding regions. The λLapA1 and λLapA2 clones correlated with the full-length LapA1 and LapA2 cDNA clones described previously (Gu, Y.-Q., et al., J. Biol. Chem. 271(24):25880 (1996)).

To determine the number of the Lap genes in the tomato genome, genomic DNA blots with single-copy reconstructions were hybridized with a $^{32}$P-labeled LapA cDNA, pDR57. pDR57 is a partial LapA1 cDNA clone that is truncated at an internal EcoR I site; it therefore does not detect 5' LapA sequences (Pautot, V., et al., Proc. Nat'l. Acad. Sci. USA 90:9906 (1993); (Gu, Y.-Q., et al., J. Biol. Chem. 271(24):25880 (1996). Three restriction enzyme digestions (Sac I, EcoR V, and EcoR I) were analyzed. VFNT genomic DNA had two fragments of 10 kb (LapA1) and 3.0 kb (LapA2) that gave strong hybridization signals; these corresponded to the intact EcoR I fragments in the four λLapA genomic clones. An additional 7-kb VFNT EcoR I fragment gave a weaker hybridization signal; this represents the LapN gene that encodes the neutral LAP proteins of tomato (Gu, Y.-Q., et al., Plant Physiol. 110:1257 (1996)).

Comparison of genomic DNA blots with VFNT and 238R DNAs indicated that the LapA2 region was polymorphic. While the 10-kb LapA1 fragment was detected in the 238R line, the 3-kb LapA2 fragment was not detected and was replaced with a 5-kb genomic fragment. This polymorphism may be due to a point mutation, small deletion, or rearrangement, and may be located near the EcoR I site that is immediately downstream from the 3' end of the LapA2 gene. This location for the polymorphism seems likely since the removal of this EcoR I site would join the adjacent 3.0-kb and 2.0-kb EcoR I fragments and produce the 5.0-kb fragment that is observed in the line 238R.

Structure of the LapA1 and LapA2 genes.

To characterize the structure of the LapA1 and LapA2 genes including the promoter sequences, the sequence for 1.4 kb of the LapA1 and LapA2 genomic clones was determined. These sequences correlated with RNAse protection data (of Example 1) and aligned with the LapA1 and LapA2 cDNA clone sequences (Gu, Y.-Q., et al., Plant Physiol. 110:1257 (1996)).

RNase protection studies were performed using two overlapping LapA1 genomic subclones and poly(A$^+$) mRNAs from wounded or healthy tomato leaves. These data indicated that exon 1 and exon 2 of LapA1 were 230 bp and 100 bp in length. When aligned with the genomic clone sequence data, the RNase protection data indicated that LapA1 and LapA2 5' UTRs (residues 1–18 of SEQ ID NO: 2 and 4), exon 1 (230 nucleotides), intron 1 (461 nucleotides) and exon 2 (93 nucleotides; partial characterization) were nearly identical at the nucleotide level. Only one base pair mismatch occurred within intron 1 and one mismatch was detected in the portion of exon 2 characterized in this study. In fact this identity continued for 86 base pairs upstream of the transcriptional initiation site. The LapA genes had a short 5'-UTR of 18 base pairs and 89% of the residues were As or Ts. Intron and exon borders were defined by the RNase protection studies and compared to the LapA1 and LapA2 cDNA sequences (Gu, Y.-Q., et al., Plant Physiol. 110:1257 (1996). The LapA exon-intron borders matched the 5'-donor and 3'-acceptor sites that constitute splice junction consensus sequences (Brown, J. W. S. Nuc. Acids Res. 14(24):9549 (1986)).

In the 0.92 kb of the LapA1 and LapA2 5'-flanking regions, several transcriptional consensus sequences were detected General transcription signals, the TATA box (−33 to −39 of SEQ ID NO:1) and the CAAT box (−116 to −119 of SEQ ID NO:1), were detected approximately 30 and 80 base pairs upstream from the transcriptional initiation site (+1) of LapA1; although in Lap A2, a TATA box was detected at residues 32–38 of SEQ ID NO:3, the CAAT box consensus was lacking. Several sequence motifs correlated with wound- and defense-response genes were found including the palindromic CACGTG motif known as the G-box. This motif is important for activity of promoters regulating genes involved in abscisic acid (ABA) and jasmonic acid (Ja) responsiveness (Guiltinan, M. J., et al., Science 250:267 (1990); Kim, S.-R., et al., Plant Physiol. 99:627 (1991)). In fact, the ABA response element (ABRE) has the consensus sequence of 5'-TCACGTGGC-3' which contains the G box motif core of ACGT (Marcotte, W. R., et al., Plant Cell 1:969 (1989)). Multiple sequences similar to the ABRE and G-box were detected in the 5'-flanking region of LapA1 and LapA2. Two overlapping ABRE-like sequences (TCACGTaGg and ggACGTaGa) were detected in both genes at positions of about −199 to −191 (ABRE1) and about −194 to −186 (ABRE2) of both SEQ ID NO:1 and 3. In addition, a G-box-like sequence, TGACaT, very similar to a JA response element was detected at position −67 to −62 of SEQ ID NO:1 and 3. A second putative regulatory sequence important for the regulation of some, but not all, ABA-responsive genes is the GC-rich rich sequence 5'-TTCACGCGCTG-3'(SEQ ID NO:12); one copy is found between nucleotides −408 to −398 of SEQ ID NO:1 in the LapA1 promoter region. Ethylene responsive elements were not detected in the 5'-flanking region of LapA1 but an ethylene box (ATTTCAAA) was noted in LapA2 (−77–777 of SEQ ID NO:3). Finally, two copies of a 10-bp motif (TCATCTTCTT; SEQ ID NO:8) that had been identified in 37 different genes that respond to abiotic or biotic stress (Goldsbrough, A. P., et al., Plant J. 3(4):563 (1993) were located −724 to −712 and −54 to −44 nucleotides upstream from the transcriptional initiation site of LapA1; only the motif adjacent to the TATA box was present in LapA2.

What is claimed is:

1. An isolated recombinant nucleic acid comprising a plant leucine aminopeptidase promoter which remains hybridized to SEQ ID NO:1 or SEQ ID NO:3 at 65° C. in 0.2× SSC for 15 minutes.

2. The isolated nucleic acid of claim 1, wherein the promoter comprises a nucleic acid subsequence corresponding to SEQ ID NO:1 or SEQ ID NO:3.

3. The isolated nucleic acid of claim 1, wherein the recombinant nucleic acid further comprises a heterologous nucleic acid subsequence operably linked to the plant leucine aminopeptidase promoter.

4. The isolated nucleic acid of claim 3, wherein the heterologous nucleic acid subsequence encodes a polypeptide selected from the group consisting of phytoalexin, chitinase, glucanase, proteinaceous protease inhibitors I and II, *Bacillus thuringiensis* δ-endotoxin, viral coat proteins, heat shock proteins (hsp), chilling acclimation response proteins (car30 and car757), acetohydroxy acid synthase, chimeric proteins of rat cytochrome p4507A1 and yeast NADPH-cytochrome P450 oxidoreductase, phosphotransferases, glutathione reductase, superoxide dismutase, malate synthetase, α amylase isozymes, and alcohol dehydrogenase.

5. The isolated nucleic acid of claim 1, wherein the nucleic acid comprises a recombinant expression cassette.

6. The isolated nucleic acid of claim 5, wherein the recombinant expression cassette further comprises an independent terminator sequence, replication sequences and a selection marker sequence.

7. An isolated recombinant nucleic acid comprising a nucleic acid sequence which encodes a polypeptide comprising residues 1–54 of SEQ ID NO:5.

8. The isolated nucleic acid of claim 7, wherein the nucleic acid encodes a full-length tomato acidic leucine aminopeptidase polypeptide comprising SEQ ID NO:5.

9. An isolated full-length recombinant genomic tomato acidic leucine aminopeptidase gene that remains hybridized to SEQ ID NO:1 or SEQ ID NO:3 at 65° C. in 0.2× SSC for 15 minutes.

10. A recombinant cell comprising the nucleic acid of claim 1.

11. The recombinant cell of claim 10, wherein the recombinant nucleic acid comprises a promoter which is operably linked to a heterologous nucleic acid.

12. The recombinant cell of claim 11, wherein the heterologous nucleic acid encodes a polypeptide selected from the group consisting of phytoalexin, chitinase, glucanase, proteinaceous protease inhibitors I and II, *Bacillus thuringiensis* δ-endotoxin, viral coat proteins, heat shock proteins (hsp), chilling acclimation response proteins (car30and car757), acetohydroxy acid synthase, chimeric proteins of rat cytochrome p4507A1 and yeast NADPH-cytochrome P450 oxidoreductase, phosphotransferases, glutathione reductase, superoxide dismutase, malate synthetase, α amylase isozymes, and alcohol dehydrogenase.

13. A transgenic plant comprising the recombinant nucleic acid of claim 1.

14. The transgenic plant of claim 13, wherein the recombinant nucleic acid comprises a promoter which is operably linked to a heterologous nucleic acid.

15. The transgenic plant of claim 13, wherein the heterologous nucleic acid encodes a polypeptide selected from the group consisting of phytoalexin, chitinase, glucanase, proteinaceous protease inhibitors I and II, *Bacillus thuringiensis* δ-endotoxin, viral coat proteins, heat shock proteins (hsp), chilling acclimation response proteins (car30 and car757), acetohydroxy acid synthase, chimeric proteins of rat cytochrome p4507A1 and yeast NADPH-cytochrome P450 oxidoreductase, phosphotransferases, glutathione reductase, superoxide dismutase, malate synthetase, α amylase isozymes, and alcohol dehydrogenase.

16. A method of expressing a nucleic acid in response to an environmental stimulus comprising the steps of:
  providing a transgenic plant comprising a recombinant expression cassette having a heterologous nucleic acid operably linked to a recombinant nucleic acid comprising a plant leucine aminopeptidase promoter which hybridizes under stringent conditions to SEQ ID NO:1 or SEQ ID NO:3; and,
  subjecting the plant to an environmental stimulus which activates the leucine aminopeptidase promoter, thereby transcribing the heterologous nucleic acid.

17. The method of claim 16, wherein the environmental stimulus is selected from the group consisting of mechanical injury, chemical injury, pathogen infection and insect infestation.

18. The method of claim 16, wherein the nucleic acid expressed in response to a environmental stimulus encodes a polypeptide selected from the group consisting of wound-induced polypeptides, peptides that signal flowering, and peptides that initiate sap production.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 935 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: -
       (B) LOCATION: 1..935
       (D) OTHER INFORMATION: /note= "tomato acidic leucine
            aminopeptidase 1 (LapA1) promoter
            region"

(xi) SEQUENCE DESCRIPTION: SEQ ID NO:1:

```
GGATCATGTA AAAATCATTT AAATAGTAAT GTTATATAAA AGATAATTAG TTAAATCAAC      60

GAATGCCTAG TGAAAATTAA AATTTAGAAA AGATTTTTTT TTGACTGATA AAAATATGTG     120

TTCCGCCAAT CTCAATTGAA AATAAATTAC ACGTGCTTAT AAATTAAACA AGATTCTAAA     180

AATCCCACAA AGGCAAGTAA TGTATATTTT TTCTTCTCCT TCTTTGTACC ACTAATTTCT     240

AAATTAATAA AACGTGTTCA AAATTTCAAC GGTGGAAACT ATTGAAAGGG ACTATAAATG     300

GTCCAATTAT TGTCCTTTAC TTATTATCCA AATAAAAGGA TGTATATCGA AATTGTATAT     360

ATATATATAT ATATATAATT CTAAACTAAT AAATTTTAAT AAGATTAATA GCGATGATGC     420

AGCGACGATG GGTTTGGTGG TGTGTGTTGA ATGAGATTAT CGATCATAAA GAAAGAGGGG     480

AGAAGATGAA CAGTTTTTTA AATAAATTTT TGGCCCAGAA AAAAACATTC ACGCGCTGAC     540

TTTAAGTGCA TTACACTCAC CTTGCCATGA CAGAGAAAAT CGTCAAAAAA TGACACAATG     600

AGACCCTACA TAAGGGTTTA AAATGAACAT CGCTGAAGCG AAATTTCGTG CCAACTTTAG     660

GTGGTCACCG ATAGGTTAGA CCTATTTTTA AAATCATCTC AATTATGTTG GTTTCTCTTC     720

AACATTGTAG GGTATCACGT AGGACGTAGA ATTATGTAGG TATCTACTTA TTCAACTTTT     780

GAATAATTTA AGCACACACT TTCTTGTGTA TATTCACAAT TGAATGACAT AGACGCGGTT     840

AAAGAGTACG AGAATGAGTA AAACGTGTTG ACATGCAAAT ATCTTGTTCT TTCTTCTATA     900

TAAGTGATGC AGAGAAAGAC TTAAGTATAC ACAAC                               935
```

(2) INFORMATION FOR SEQ ID NO:2:

(i) SEQUENCE CHARACTERISTICS:
       (A) LENGTH: 1929 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: -
       (B) LOCATION: 1..1929
       (D) OTHER INFORMATION: /note= "tomato acidic leucine
            aminopeptidase 1 (LapA1) cDNA"

(ix) FEATURE:
       (A) NAME/KEY: CDS
       (B) LOCATION: 19..1734
       (D) OTHER INFORMATION: /product= "acidic leucine aminopeptidase 1 (LapA1)"

(xi) SEQUENCE DESCRIPTION: SEQ ID NO:2:

```
AAATTTTCTT TATTTACAAT GGCAACACTA AGAGTTTCTT CATTGTTTGC TTCTTCTTCT        60
TCATCTTTGC ATTCTAACCC TTCAGTTTTT ACTAAATATC AATCTAGTCC CAAATGGGCT       120
TTTTCATTTC CAGTTACACC CTTGTGTTCA AAAAGAAGTA AAAGAATAGT TCATTGCATT       180
GCTGGTGATA CTCTTGGTCT TACTAGGCCT AATGAAAGTG ATGCCCCTAA GATATCAATT       240
GGTGCTAAAG ATACTGCTGT GGTGCAATGG CAAGGAGACT TACTTGCAAT AGGCGCGACG       300
GAGAATGACA TGGCTAGAGA TGAGAATTCT AAGTTCAAGA ATCCACTATT GCAACAGCTT       360
GATTCCGAAT TGAATGGTTT ATTGTCTGCA GCTTCTTCTG AGGAGGATTT TAGCGGAAAG       420
TCTGGACAAT CCGTAAATCT CAGGTTTCCT GGTGGAAGGA TTACTCTAGT TGGTCTTGGC       480
TCATCAGCAT CATCACCTAC TTCTTATCAC AGTTTAGGAC AGGCTGCTGC TGCTGCTGCC       540
AAGTCTTCTC AGGCTCGTAA TATTGCCGTT GCACTTGCTT CCACCGATGG ACTCTCTGCA       600
GAATCGAAGA TTAACTCTGC CTCTGCCATA GCAACTGGAG TTGTGCTAGG GTCATTTGAA       660
GATAATAGGT TTAGGTCCGA GTCGAAGAAA TCAACTTTGG AATCTTTGGA TATTCTTGGA       720
CTGGGAACTG GACCTGAAAT AGAGAGGAAA ATCAAGTATG CAGAACATGT ATGTGCAGGT       780
GTTATACTCG GTAGAGAGCT CGTTAACGCA CCAGCCAATA TAGTTACGCC TGCGGTACTT       840
GCTGAAGAGG CTAAAAAGAT TGCGTCCACT TATAGCGATG TCATTTCTGT TAACATTTTG       900
GATGCTGAGC AGTGCAAAGA ATTGAAAATG GGAGCCTACT TAGCTGTTGC TGCAGCAGCT       960
ACTGAAAATC CTCCTTACTT CATCCATTTA TGTTTTAAAA CTCCTACTAA GGAACGCAAA      1020
ACAAAGTTAG CCTTGGTTGG AAAGGGATTA ACTTTTGACA GTGGTGGCTA CAACCTCAAG      1080
GTCGGAGCTC GTTCGAGGAT TGAGCTAATG AAGAATGACA TGGGAGGGGC TGCTGCTGTT      1140
TTAGGTGCAG CAAAAGCTCT TGGTGAAATT AGGCCTTCCA GAGTAGAGGT GCATTTCATT      1200
GTCGCAGCAT GTGAAAATAT GATCAGTGCA GAAGGCATGA GGCCTGGAGA CATTGTCACA      1260
GCTTCAAATG GTAAGACAAT TGAGGTTAAC AATACTGATG CTGAGGGTAG GCTCACACTT      1320
GCTGATGCTT TGATATATGC CTGTAACCAA GGTGTTGAGA AGATAATTGA TCTGGCAACA      1380
TTAACTGGTG CTATTATGGT TGCTCTTGGA CCTTCAGTTG CTGGTGCTTT TACACCTAAT      1440
GATGACCTAG CAAGGGAGGT TGTTGAAGCT GCTGAGGCAA GTGGTGAAAA ACTATGGAGG      1500
ATGCCTATGG AGGAGAGTTA CTGGGAGAGT ATGAAATCAG GAGTGGCTGA TATGATTAAC      1560
ACGGGGCCTG GTAATGGCGG TGCTATAACT GGTGCTCTCT TCCTCAAACA ATTTGTCGAC      1620
GAGAAGGTTC AGTGGTTGCA TCTCGATGTA GCTGGCCCCG TATGGAGCGA TGAAAAGAAA      1680
AACGCCACGG GTTATGGTGT TTCAACTCTG GTGGAATGGG TGCTGAGGAA CTAGTCAAGA      1740
TGTTGATGGC TAAACATATT AGGGACTAAT GATGTTTGGA AAATAAATG CATCAAGTTG       1800
TATGAATAAA GGCAATAGTA TAGGCTTTCT TGTTATCTTG ATTAATAAAA TGCCTAAATA      1860
AAATTGCCAC TTTACCTTTT GAAATGAAAT TTATTATTCC CGTCTTAAAA AAAAAAAAA      1920
AAAAAAAA                                                              1929
```

(2) INFORMATION FOR SEQ ID NO:3:

(i) SEQUENCE CHARACTERISTICS:
    (A) LENGTH: 1177 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: -
    (B) LOCATION: 1..1177
    (D) OTHER INFORMATION: /note= "tomato acidic leucine
        aminopeptidase 2 (LapA2) promoter
        region"

(xi) SEQUENCE DESCRIPTION: SEQ ID NO:3:

```
CTTATGCTTT CGAAATTATC AATTCTAGTT TTGAATTTAT ATGGAAATGA GATAAATTAA      60

ATGATGATAC CTTCAAAATT TTGATCTTCT TAGAAAAATA ATTAGTTTTG TTATCAATAA     120

CTCAATAAAG TCTAAAAAAT AGAATTATTT TGGAAAGTAA GAAATTTGAC CCCTTAAGAA     180

GAAGAAAAGA GAAATACTTA ACTTGATATA TAGGTGTGGG GTTAGGTGAG GATAAGAGGT     240

GAAGAAGAAG AAATAAAGAA AGAAAATGGA GGGAGCTTGA AAGTTGGGAT GGAAAATGAT     300

TTAAAATTTG AAATGAAATA AAATTAAAAT TAATAAAATT AAAATAAGTC AAAAAGTAAG     360

ACAAAGAAAT AAAGAAAAAC TTAAAATGAA AAAAAATAAT ATTTCAAATT GATTTAACAC     420

GTGTCACACA ATGATTGGTG TGTGATTCCA CTTGCCATTT AAAATCTGGA ATTGTTCCAA     480

AAATGATGTA ATAATATATG TCCGGAATAC TTTAGAGGGG TAATAGGACA TCTGCATAGT     540

TAAGGTGTCT TTTTTAAAAA TTCAGGACAA CTTCAGGTGT CACTTTATGA CTTCTCTCTC     600

TATATATAAG TAATTCTAAA CTAATGATTT TAAATAAGAT TAATAGCGAT GATGCAGTGA     660

TGGTGGGTTA GTGGTGTGTG TTGAATGAGA TTATCACAAA GAAAGAGGGA AGAAGATGAA     720

CAATTTTTTA AAATAAATTT TTGGCTCGAA AAAAAATATT TACGCGCTGA CTTTGAGTGC     780

ATACACTCAC CTTGCCATGA CAGCGAAAAG CGTCAAAAAT GACACAACGA GACCCTACAT     840

AAGGGATTTA AAATGAACAT CGCAGAATTG AAGTGTCTAA GCGAAATTCC GTGCAACTTT     900

TAGGTGGTTA CCGATAGGTT AGACCTATTT TTAAAATCAT CTCAATTATG TTGGTTTCTC     960

TTCAACATTG TAGGGTATCA CGTAGGACGT AGAATTATGT AGGTATCTAC TTATTCAACT    1020

TTTGAATAGT TTAAGCACGC ACTTGCTTGT GTATATTCAA AATTGAATGA CATAGACGCG    1080

GTTAAAGAGT AGAGAATGAG TAAAACGTGT TGACATGCAA ATATCTTGTT CTTTCTTCTA    1140

TATAAGTGAT GCAGAGAAAG ACTTAAGTAT ACACAAC                             1177
```

(2) INFORMATION FOR SEQ ID NO:4:

(i) SEQUENCE CHARACTERISTICS:
        (A) LENGTH: 1971 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1971
        (D) OTHER INFORMATION: /note= "tomato acidic leucine
            aminopeptidase 2 (LapA2) cDNA"

(xi) SEQUENCE DESCRIPTION: SEQ ID NO:4:

```
GTTTCTTCAT TGTTTGCTTC TTCTTCTTCA TCTTTGCATT CTAACCCTTC AGTTTTTACT      60

AAATATCAAT CTAGTCCCAA ATGGGCTTTT TCATTTCCAG TTACACCCTT GTGTTCAAAA     120

AGAAGTAAAA GAATAGTTCA TTGCATTGCT GGTGATACTC TTGGTCTTAC TAGGCCTAAT     180

GAAAGTGATG CCCCTAAGAT ATCAATTGGT GCTAAAGATA CTGCTGTGGT GCAATGGCAA     240

GGAGACTTAC TTGCAATAGG CGCGACGGAG AATGACATGG CTAGAGATGA GAATTCTAAG     300

TTCAAGAATC CACTATTGCA ACAGCTTGAT TCCGAATTGA ATGGTTTATT GTCTGCAGCT     360
```

```
TCTTCTGAGG AGGATTTTAG CGGAAAGTCT GGACAATCCG TAAATCTCAG GTTTCCTGGT    420

GGAAGGATTA CTCTAGTTGG TCTTGGCTCA TCAGCATCAT CACCTACTTC TTATCACAGT    480

TTAGGACAGG CTGCTGCTGC TGCTGCCAAG TCTTCTCAGG CTCGTAATAT TGCCGTTGCA    540

CTTGCTTCCA CCGATGGACT CTCTGCAGAA TCGAAGATTA ACTCTGCCTC TGCCATAGCA    600

ACTGGAGTTG TGCTAGGGTC ATTTGAAGAT AATAGGTTTA GGTCCGAGTC GAAGAAATCA    660

ACTTTGGAAT CTTTGGATAT TCTTGGACTG GAACTGGAC CTGAAATAGA GAGGAAAATC    720

AAGTATGCAG AACATGTATG TGCAGGTGTT ATACTCGGTA GAGAGCTCGT TAACGCACCA    780

GCCAATATAG TTACGCCTGC GGTACTTGCT GAAGAGGCTA AAAAGATTGC GTCCACTTAT    840

AGCGATGTCA TTTCTGTTAA CATTTTGGAT GCTGAGCAGT GCAAAGAATT GAAAATGGGA    900

GCCTACTTAG CTGTTGCTGC AGCAGCTACT GAAAATCCTC CTTACTTCAT CCATTTATGT    960

TTTAAAACTC CTACTAAGGA ACGCAAAACA AAGTTAGCCT TGGTTGGAAA GGGATTAACT   1020

TTTGACAGTG GTGGCTACAA CCTCAAGGTC GGAGCTGGTT CGAGGATTGA GCTAATGAAG   1080

AATGACATGG GAGGGGCTGC TGCTGTTTTA GGTGCAGCAA AAGCTCTTGG TGAAATTAGG   1140

CCTTCCAGAG TAGAGGTGCA TTTCATTGTC GCAGCATGTG AAAATATGAT CAGTGCAGAA   1200

GGCATGAGGC CTGGAGACAT TGTCACAGCT TCAAATGGTA AGACAATTGA GGTTAACAAT   1260

ACTGATGCTG AGGGTAGGCT CACACTTGCT GATGCTTTGA TATATGCCTG TAACCAAGGT   1320

GTTGAGAAGA TAATTGATCT GGCAACATTA ACTGGTGCTA TTATGGTTGC TCTTGGACCT   1380

TCAGTTGCTG GTGCTTTTAC ACCTAATGAT GACCTAGCAA GGGAGGTTGT TGAAGCTGCT   1440

GAGGCAAGTG GTGAAAAACT ATGGAGGATG CCTATGGAGG AGAGTTACTG GGAGAGTATG   1500

AAATCAGGTG TGGCTGATAT GATTAACTTG GGACCTGGTA ATGGCGGTGC TATAACTGGT   1560

GCTCTCTTCC TCAAACAATT TGTTGACGAG AAGGTTCAGT GGTTGCATCT CGACGTAGCT   1620

GGCCCCGTAT GGAGCGATGA AAAGAAAAAC GCCACGGGTT ATGGTGTTTC AACTCTGGTG   1680

GAATGGGTGC TGAGGAACTA GTCAAGATGT TGATGGCTAA GCATATTAGG GACTCATGAT   1740

GTTTGAGAAA ATAAATGCAT CAAGTTGTAT GAATAAAGGC AATAGAATAG GCTTTCTTGT   1800

TTTCTAGATG AATAAAATGC CTAAATAAAA TTGCCACTTT ACCTTTTCAA ATGAAATTTA   1860

TTATTCCCGT CTTATTTACG TATGTCTGAT AGAGATTATA TTCACTCTAG TATCGTAACT   1920

TGGAGATGAA AGTGATAAAA AAAAAAAAAA AAAAAAAAAA AAAAAAAAAA A           1971
```

(2) INFORMATION FOR SEQ ID NO:5:

(i) SEQUENCE CHARACTERISTICS:
        (A) LENGTH: 571 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..571
        (D) OTHER INFORMATION: /note= "deduced full-length protein
           sequence of acidic leucine
           aminopeptidase (LapA1) protein from
           tomato"

(xi) SEQUENCE DESCRIPTION: SEQ ID NO:5:

```
Met Ala Thr Leu Arg Val Ser Ser Leu Phe Ala Ser Ser Ser Ser
1               5                   10                  15

Leu His Ser Asn Pro Ser Val Phe Thr Lys Tyr Gln Ser Ser Pro Lys
```

-continued

```
                    20                  25                  30
Trp Ala Phe Ser Phe Pro Val Thr Pro Leu Cys Ser Lys Arg Ser Lys
                35                  40                  45
Arg Ile Val His Cys Ile Ala Gly Asp Thr Leu Gly Leu Thr Arg Pro
             50                  55                  60
Asn Glu Ser Asp Ala Pro Lys Ile Ser Ile Gly Ala Lys Asp Thr Ala
 65                  70                  75                  80
Val Val Gln Trp Gln Gly Asp Leu Leu Ala Ile Gly Ala Thr Glu Asn
                 85                  90                  95
Asp Met Ala Arg Asp Glu Asn Ser Lys Phe Lys Asn Pro Leu Leu Gln
                100                 105                 110
Gln Leu Asp Ser Glu Leu Asn Gly Leu Leu Ser Ala Ala Ser Ser Glu
                115                 120                 125
Glu Asp Phe Ser Gly Lys Ser Gly Gln Ser Val Asn Leu Arg Phe Pro
            130                 135                 140
Gly Gly Arg Ile Thr Leu Val Gly Leu Gly Ser Ser Ala Ser Ser Pro
145                 150                 155                 160
Thr Ser Tyr His Ser Leu Gly Gln Ala Ala Ala Ala Ala Lys Ser
                165                 170                 175
Ser Gln Ala Arg Asn Ile Ala Val Ala Leu Ala Ser Thr Asp Gly Leu
                180                 185                 190
Ser Ala Glu Ser Lys Ile Asn Ser Ala Ser Ala Ile Ala Thr Gly Val
                195                 200                 205
Val Leu Gly Ser Phe Glu Asp Asn Arg Phe Arg Ser Glu Ser Lys Lys
                210                 215                 220
Ser Thr Leu Glu Ser Leu Asp Ile Leu Gly Leu Gly Thr Gly Pro Glu
225                 230                 235                 240
Ile Glu Arg Lys Ile Lys Tyr Ala Glu His Val Cys Ala Gly Val Ile
                245                 250                 255
Leu Gly Arg Glu Leu Val Asn Ala Pro Ala Asn Ile Val Thr Pro Ala
                260                 265                 270
Val Leu Ala Glu Ala Lys Lys Ile Ala Ser Thr Tyr Ser Asp Val
                275                 280                 285
Ile Ser Val Asn Ile Leu Asp Ala Glu Gln Cys Lys Glu Leu Lys Met
                290                 295                 300
Gly Ala Tyr Leu Ala Val Ala Ala Ala Thr Glu Asn Pro Pro Tyr
305                 310                 315                 320
Phe Ile His Leu Cys Phe Lys Thr Pro Thr Lys Glu Arg Lys Thr Lys
                325                 330                 335
Leu Ala Leu Val Gly Lys Gly Leu Thr Phe Asp Ser Gly Gly Tyr Asn
                340                 345                 350
Leu Lys Val Gly Ala Arg Ser Arg Ile Glu Leu Met Lys Asn Asp Met
                355                 360                 365
Gly Gly Ala Ala Ala Val Leu Gly Ala Ala Lys Ala Leu Gly Glu Ile
                370                 375                 380
Arg Pro Ser Arg Val Glu Val His Phe Ile Val Ala Ala Cys Glu Asn
385                 390                 395                 400
Met Ile Ser Ala Glu Gly Met Arg Pro Gly Asp Ile Val Thr Ala Ser
                405                 410                 415
Asn Gly Lys Thr Ile Glu Val Asn Asn Thr Asp Ala Glu Gly Arg Leu
                420                 425                 430
Thr Leu Ala Asp Ala Leu Ile Tyr Ala Cys Asn Gln Gly Val Glu Lys
                435                 440                 445
```

```
Ile Ile Asp Leu Ala Thr Leu Thr Gly Ala Ile Met Val Ala Leu Gly
    450                 455                 460
Pro Ser Val Ala Gly Ala Phe Thr Pro Asn Asp Asp Leu Ala Arg Glu
465                 470                 475                 480
Val Val Glu Ala Ala Glu Ala Ser Gly Glu Lys Leu Trp Arg Met Pro
                485                 490                 495
Met Glu Glu Ser Tyr Trp Glu Ser Met Lys Ser Gly Val Ala Asp Met
            500                 505                 510
Ile Asn Thr Gly Pro Gly Asn Gly Gly Ala Ile Thr Gly Ala Leu Phe
        515                 520                 525
Leu Lys Gln Phe Val Asp Glu Lys Val Gln Trp Leu His Leu Asp Val
    530                 535                 540
Ala Gly Pro Val Trp Ser Asp Glu Lys Lys Asn Ala Thr Gly Tyr Gly
545                 550                 555                 560
Val Ser Thr Leu Val Glu Trp Val Leu Arg Asn
                565                 570
```

(2) INFORMATION FOR SEQ ID NO:6:

(i) SEQUENCE CHARACTERISTICS:
        (A) LENGTH: 565 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..565
        (D) OTHER INFORMATION: /note= "deduced partial protein
            sequence of acidic leucine aminopeptidase 2
            (LapA2) from tomato"

(xi) SEQUENCE DESCRIPTION: SEQ ID NO:6:

```
Ser Ser Leu Phe Ala Ser Ser Ser Ser Leu His Ser Asn Pro Ser
1               5                   10                  15
Val Phe Thr Lys Tyr Gln Ser Ser Pro Lys Trp Ala Phe Ser Phe Pro
                20                  25                  30
Val Thr Pro Leu Cys Ser Lys Arg Ser Lys Arg Ile Val His Cys Ile
            35                  40                  45
Ala Gly Asp Thr Leu Gly Leu Thr Arg Pro Asn Glu Ser Asp Ala Pro
50                  55                  60
Lys Ile Ser Ile Gly Ala Lys Asp Thr Ala Val Val Gln Trp Gln Gly
65                  70                  75                  80
Asp Leu Leu Ala Ile Gly Ala Thr Glu Asn Asp Met Ala Arg Asp Glu
                85                  90                  95
Asn Ser Lys Phe Lys Asn Pro Leu Leu Gln Gln Leu Asp Ser Glu Leu
            100                 105                 110
Asn Gly Leu Leu Ser Ala Ala Ser Glu Glu Asp Phe Ser Gly Lys
        115                 120                 125
Ser Gly Gln Ser Val Asn Leu Arg Phe Pro Gly Gly Arg Ile Thr Leu
        130                 135                 140
Val Gly Leu Gly Ser Ser Ala Ser Ser Pro Thr Ser Tyr His Ser Leu
145                 150                 155                 160
Gly Gln Ala Ala Ala Ala Ala Lys Ser Ser Gln Ala Arg Asn Ile
                165                 170                 175
Ala Val Ala Leu Ala Ser Thr Asp Gly Leu Ser Ala Glu Ser Lys Ile
            180                 185                 190
```

```
Asn Ser Ala Ser Ala Ile Ala Thr Gly Val Val Leu Gly Ser Phe Glu
            195                 200                 205

Asp Asn Arg Phe Arg Ser Glu Ser Lys Lys Ser Thr Leu Glu Ser Leu
210                 215                 220

Asp Ile Leu Gly Leu Gly Thr Gly Pro Glu Ile Glu Arg Lys Ile Lys
225                 230                 235                 240

Tyr Ala Glu His Val Cys Ala Gly Val Ile Leu Gly Arg Glu Leu Val
                245                 250                 255

Asn Ala Pro Ala Asn Ile Val Thr Pro Ala Val Leu Ala Glu Glu Ala
                260                 265                 270

Lys Lys Ile Ala Ser Thr Tyr Ser Asp Val Ile Ser Val Asn Ile Leu
                275                 280                 285

Asp Ala Glu Gln Cys Lys Glu Leu Lys Met Gly Ala Tyr Leu Ala Val
            290                 295                 300

Ala Ala Ala Ala Thr Glu Asn Pro Pro Tyr Phe Ile His Leu Cys Phe
305                 310                 315                 320

Lys Thr Pro Thr Lys Glu Arg Lys Thr Lys Leu Ala Leu Val Gly Lys
                325                 330                 335

Gly Leu Thr Phe Asp Ser Gly Gly Tyr Asn Leu Lys Val Gly Ala Gly
                340                 345                 350

Ser Arg Ile Glu Leu Met Lys Asn Asp Met Gly Gly Ala Ala Ala Val
            355                 360                 365

Leu Gly Ala Ala Lys Ala Leu Gly Glu Ile Arg Pro Ser Arg Val Glu
370                 375                 380

Val His Phe Ile Val Ala Ala Cys Glu Asn Met Ile Ser Ala Glu Gly
385                 390                 395                 400

Met Arg Pro Gly Asp Ile Val Thr Ala Ser Asn Gly Lys Thr Ile Glu
                405                 410                 415

Val Asn Asn Thr Asp Ala Glu Gly Arg Leu Thr Leu Ala Asp Ala Leu
                420                 425                 430

Ile Tyr Ala Cys Asn Gln Gly Val Glu Lys Ile Ile Asp Leu Ala Thr
            435                 440                 445

Leu Thr Gly Ala Ile Met Val Ala Leu Gly Pro Ser Val Ala Gly Ala
450                 455                 460

Phe Thr Pro Asn Asp Asp Leu Ala Arg Glu Val Val Glu Ala Ala Glu
465                 470                 475                 480

Ala Ser Gly Glu Lys Leu Trp Arg Met Pro Met Glu Glu Ser Tyr Trp
                485                 490                 495

Glu Ser Met Lys Ser Gly Val Ala Asp Met Ile Asn Leu Gly Pro Gly
            500                 505                 510

Asn Gly Gly Ala Ile Thr Gly Ala Leu Phe Leu Lys Gln Phe Val Asp
            515                 520                 525

Glu Lys Val Gln Trp Leu His Leu Asp Val Ala Gly Pro Val Trp Ser
530                 535                 540

Asp Glu Lys Lys Asn Ala Thr Gly Tyr Gly Val Ser Thr Leu Val Glu
545                 550                 555                 560

Trp Val Leu Arg Asn
                565

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear
```

(ii) MOLECULE TYPE: peptide (ix) FEATURE:
            (A) NAME/KEY: Peptide
            (B) LOCATION: 1..6
            (D) OTHER INFORMATION: /note= "first 6 N-terminal amino acids
                from deduced protein sequence of acidic leucine
                aminopeptidase 1 (LapA1) from tomato believed to be
                N-terminal amino acids of acidic leucine aminopeptidase 2
                (LapA2) "

(xi) SEQUENCE DESCRIPTION: SEQ ID NO:7:

Met Ala Thr Leu Arg Val
1               5

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..20
        (D) OTHER INFORMATION: /note= "left lambda-gt11 primer"

(xi) SEQUENCE DESCRIPTION: SEQ ID NO:8:

TGGCGACGAC TCTGGAGCCG                                                    20

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "right lambda-gt11 primer"

(xi) SEQUENCE DESCRIPTION: SEQ ID NO:9:

TGACACCAGA CCAACTGGTA ATGG                                               24

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Ile Ala Gly Asp Thr Leu
1               5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS:

-continued (D) TOPOLOGY: linear (ii) MOLECULE TYPE: peptide (xi) SEQUENCE DESCRIPTION: SEQ ID NO:11:

Gly Asp Thr Leu Gly Leu
1               5

(2) INFORMATION FOR SEQ ID NO:12:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TTCACGCGCT G                                                         11

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TCATCTTCTT                                                           10